United States Patent
Saeed et al.

(10) Patent No.: US 11,958,927 B2
(45) Date of Patent: Apr. 16, 2024

(54) INTRAOCULAR DEVICES

(71) Applicant: UEA Enterprises Limited, Norwich (GB)

(72) Inventors: Aram Saeed, Norwich (GB); Michael Wormstone, Norwich (GB)

(73) Assignee: UEA Enterprises, Limited, Norwich (GB)

( * ) Notice: Subject to any disclaimer, the term of this patent is extended or adjusted under 35 U.S.C. 154(b) by 211 days.

(21) Appl. No.: 17/274,096

(22) PCT Filed: Sep. 5, 2019

(86) PCT No.: PCT/GB2019/052479
§ 371 (c)(1),
(2) Date: Mar. 5, 2021

(87) PCT Pub. No.: WO2020/049307
PCT Pub. Date: Mar. 12, 2020

(65) Prior Publication Data
US 2021/0198408 A1    Jul. 1, 2021

(30) Foreign Application Priority Data
Sep. 6, 2018 (GB) .................... 1814535

(51) Int. Cl.
*B33Y 10/00* (2015.01)
*A61F 2/16* (2006.01)
(Continued)

(52) U.S. Cl.
CPC ............ *C08F 283/065* (2013.01); *A61F 2/16* (2013.01); *A61L 27/16* (2013.01); *B29C 64/124* (2017.08);
(Continued)

(58) Field of Classification Search
CPC ..... A61L 2430/16; A61L 27/16; B33Y 10/00; B33Y 40/20; B33Y 80/00; B29C 64/35; B29C 64/124
See application file for complete search history.

(56) References Cited

U.S. PATENT DOCUMENTS

| 5,476,749 A | 12/1995 | Steinmann et al. |
| 2007/0010883 A1* | 1/2007 | Mentak ................. G02B 1/043 526/329.2 |

(Continued)

FOREIGN PATENT DOCUMENTS

| CN | 106362215 A | 2/2017 |
| WO | 9640303 | 12/1996 |
| WO | 2015022511 A1 | 2/2015 |

OTHER PUBLICATIONS

International Search Report and Written Opinion from corresponding PCT Application No. PCT/GB2019/052479 dated Dec. 5, 2019.
(Continued)

*Primary Examiner* — Nahida Sultana
(74) *Attorney, Agent, or Firm* — Greer, Burns & Crain, Ltd.

(57) ABSTRACT

Described herein are methods of stereolithographically printing intraocular devices, in particular intraocular lenses, as well as stereolithographic compositions for use therein. The stereolithography composition may comprise: a photoinitiator; a monofunctional aryl acrylate monomer, wherein the acrylate group of the monofunctional aryl acrylate monomer is of the formula -O-(C=O)-CH=CH$_2$; and a multifunctional methacrylate or acrylate cross-linker, wherein the monofunctional aryl acrylate monomer is present in the composition in a greater amount than the multifunctional methacrylate or acrylate cross-linker.

20 Claims, 5 Drawing Sheets

(51) Int. Cl.
    *A61L 27/16*     (2006.01)
    *B29C 64/124*     (2017.01)
    *B29C 64/35*     (2017.01)
    *B29D 11/02*     (2006.01)
    *B33Y 40/20*     (2020.01)
    *B33Y 70/00*     (2020.01)
    *B33Y 80/00*     (2015.01)
    *C08F 283/06*     (2006.01)
    *B29K 105/00*     (2006.01)

(52) U.S. Cl.
    CPC ............ *B29C 64/35* (2017.08); *B29D 11/023* (2013.01); *B33Y 10/00* (2014.12); *B33Y 40/20* (2020.01); *B33Y 70/00* (2014.12); *B33Y 80/00* (2014.12); *A61F 2002/1681* (2013.01); *A61F 2240/001* (2013.01); *B29K 2105/0002* (2013.01)

(56) References Cited

U.S. PATENT DOCUMENTS

| | | | |
|---|---|---|---|
| 2009/0250828 A1 | 10/2009 | Rosen et al. | |
| 2010/0168356 A1* | 7/2010 | Lai | A61L 27/16 526/239 |
| 2012/0309899 A1 | 12/2012 | Akinay et al. | |
| 2014/0213733 A1 | 7/2014 | Schlueter | |
| 2015/0073549 A1* | 3/2015 | Webb | B29C 39/10 264/1.7 |
| 2018/0221141 A1 | 8/2018 | Gonzalez | |
| 2020/0009787 A1* | 1/2020 | Billiet | B29B 17/0005 |
| 2020/0283548 A1* | 9/2020 | Stansbury | C08F 220/1811 |

OTHER PUBLICATIONS

Zhang, Biao, et al., Reprocessable thermosets for sustainable three-dimensional printing, Nature Communications, 2018, 9:1831.

Search Report from Corresponding application No. GB1814535.9 dated Mar. 11, 2019.

Eldred, Julie A., et al., An In Vitro Evaluation of the Anew Zephyr Open-Bag IOL in the Prevention of Posterior Capsule Opacification Using a Human Capsular Bag Model, Invest Ophthalmol Vis.Sci. 2014, 55, 7057-7064.

Aliancy, Joah et al., Long-term capsule clarity with a disk-shaped intraocular lens, https://doi.org/10.1016/j.icrs.2017.12.029.

Zhou, Fan et al., Additive Manufacturing of a 3D Terahertz Gradient-Refractive Index Lens, Adv. Optical Mater., 2016.

Kumagai, Hiroaki et al, Modeling the transparent shape memory gels by 3D printer Acculas, Nanosenors, Biosensors and Info-Tech Sensors and Systems, 2016.

Debellemanière, Guillaume, et al., Three-dimensional Printing of Optical Lenses and Ophthalmic Surgery: Challenges and Perspectives, Journal of Refractive Surgery, vol. 32, No. 3, 2016.

Debellemanière, Guillaume, et al., Optical and morphological characterization of a 3D printed intraocular lens, Acta Ophthalmologica, vol. 92, Issue s253, 2014. (Abstract only).

UEA data sheet Intraocular lens design—the use of rapid 3D printing, https://www.uea.ac.uk/business/licensing-opportunities/medical-and-life-sciences-intr., printed Jun. 22, 2018.

Flintbox data sheet, Customizable 3D printed accomodating intraocular lens, posted Mar. 12, 2018.

Alcon Acrysof IA, Aspheric IOL—product information booklet, Alcon Industries, 2005, 2007, 2010 Alcon, Inc.

\* cited by examiner

INTRAOCULAR DEVICES

This application is a U.S. National Phase under 35 U.S.C. § 371 of International Application No. PCT/GB2019/052479, filed Sep. 5, 2019, which claims priority to GB Application No. 1814535.9, filed Sep. 6, 2018.

FIELD OF THE INVENTION

This invention is directed to methods of stereolithographically printing intraocular devices, in particular intraocular lenses, as well as stereolithographic compositions for use therein.

BACKGROUND OF THE INVENTION

Cataract, the opacification of the crystalline lens in the eye, is the leading cause of blindness worldwide. While this disease is most commonly associated with age, other factors such as diabetes, exposure to UV radiation or smoking can result in the development of this disorder. All these circumstances lead to the degradation of proteins in the lens fibres, which aggregate and scatter the light, causing loss of vision. Currently, the only treatment available for cataract is surgery with implantation of an intraocular lens (IOL) to restore vision. While considerable advances have been made on the surgical technique and treatment, it remains a problem due to the high occurrence of secondary cataract. This disorder, also known as posterior capsule opacification (PCO), is caused by a wound-healing response in the lens epithelial cells (LECs) left in the capsular bag after surgery. These cellular processes result in proliferation, transdifferentiation, migration of the cells onto the posterior capsule, matrix deposition and fibre cell differentiation. Consequently, the capsular bag is wrinkled and opacified, causing the visual impairment characteristic of PCO. Although vision can be recovered by performing a Nd:YAG laser surgery, this is highly likely to trigger a wide variety of ocular complications. Thus, current research is focusing on trying to find a way to prevent this disorder. This can be achieved by developing IOL biomaterials and designs that can prevent PCO by modulating cell adhesion and migration. Moreover, drugs can be incorporated in the IOL to block the cellular signalling routes that lead to the onset of PCO. However, the moulding-based manufacture techniques currently available do not allow for rapid and cost-effective production of IOLs. This represents a hurdle in the research for methods for prevention of PCO, so it is fundamental to seek alternative technologies for manufacturing IOLs.

Currently, a wide variety of materials are used in the fabrication of IOLs; the materials can be rigid hydrophobic materials such as polymethylmethacrylate (PMMA) or flexible and foldable materials such as acrylics, silicones and hydrogels. The flexible materials may be deformable and foldable to allow implantation of the IOL through a smaller incision and are therefore preferable to rigid IOLs. Similarly, there are different IOL designs including single piece or multipiece designs, plate or open loop styles, and angulated or planar haptic designs. However, although a variety of IOL designs are available, the methods of fabrication are limited.

Currently, IOLs are manufactured using either a moulding or lathing technique. In moulding techniques, a curable material is introduced into the cavity of a polished stainless steel mould that has the specific design and shape required to achieve the desired refraction of light for a particular material and then the curable material is cured. However, moulding processes are labour intensive and some curable materials can leave residue on the mould which requires removal with specialist cleaning processes, resulting in downtime for the moulding and fabrication process and leading to increased production costs. Moreover, batch to batch variation caused by damage to the moulds and normal wear and tear, requiring mould replacement, also results in increased production costs. More seriously, the gap between the halves of the mould during the curing process can result in material leaking out of the mould and potentially generating defects around the edge of the IOL, such as sharp edges, which, if not removed (by, for example, polishing), can cause damage during implantation of the IOL in the capsular bag. Although some of these issues have been addressed, the solutions have contributed to increasing the cost of production and extended the lead time prior to IOLs reaching patients, in particular, during prototyping processes for new IOL designs.

In lathing techniques, a sheet of blank lenses is cast to form the material for the IOL, a process that often involves curing the material by polymerisation (frequently, thermal polymerisation). The sheets of blank lenses are then cut with a lathe to form the optic of the IOL, whilst maintaining the temperature of the sheet at or below 0° C. The lathing process often then involves cutting, grinding, drilling and machining operations to achieve the finished IOL. After the lathing process has been used to produce the optic, the haptic (or haptics) must be attached by first drilling on both sides of the optic and then inserting and fixing the haptic(s) in place. Although the lathing process can avoid some of the problems associated with moulding processes, it is also labour intensive and requires multiple steps. Additionally, the formation of a void during the casting and polymerisation stage of the process has been reported and, although these voids do not affect the quality of vision, they do affect the contrast sensitivity of the IOL. Moreover, for more complex designs of IOL, extensive lathing processes are required which can contribute to increasing the cost of production.

Three-dimensional (3D) printing, is a tooling technology that builds objects by adding the starting material layer by layer, as dictated by a software file, for example, an STL file, that describes a computer model of the object, which may have been created on computer-aided design (CAD) software. After its invention in the 1980s a wide variety of industries have taken advantage of its versatility, speed and reduced cost. Biomedical research is also benefitting from this technology in areas such as tissue engineering and drug delivery because it allows for rapid and personalised production of implants, scaffolds, tablets or models for surgery, to name a few.

Attempts have been made to use 3D printing to produce intraocular lenses. The lenses were printed using a LUXeXcel printer. This 3D printer uses inkjet technology to jet tiny droplets of a UV-curable acrylic-based material (a polymethylmethacrylate-like photopolymer material) onto a surface, curing the resin using UV light. Unfortunately, the 3D printed lenses produced using this technique do not have the required optical quality for such lenses. For example, the 3D printed lenses show significant changes in focal length relative to lenses of the same shape produced by traditional techniques. Additionally, the surface roughness of these 3D printed lenses does not meet the criteria for potentially implantable intraocular devices.

The present inventors have found that examples of the invention as described herein avoid or at least mitigate at least one of the difficulties described above.

SUMMARY

In an aspect, there is provided a stereolithography composition for printing intraocular devices, the stereolithography composition comprising:
- a photoinitiator;
- a monofunctional aryl acrylate monomer, wherein the acrylate group of the monofunctional aryl acrylate monomer is of the formula —O—(C=O)—CH=CH$_2$; and
- a multifunctional methacrylate or acrylate cross-linker,
- wherein the monofunctional aryl acrylate monomer is present in the composition in a greater amount than the multifunctional methacrylate or acrylate cross-linker.

In another aspect, there is provided a stereolithography composition for printing intraocular devices, the stereolithography composition comprising:
- a photoinitiator;
- a monofunctional aryl acrylate monomer, wherein the acrylate group of the monofunctional aryl acrylate monomer is of the formula —O—(C=O)—CH=CH$_2$; and
- a multifunctional methacrylate cross-linker,
- wherein the monofunctional aryl acrylate monomer is present in the composition in a greater amount than the multifunctional methacrylate cross-linker.

In a further aspect, there is provided a method of producing intraocular devices, the method comprising:
- stereolithographically printing intraocular devices using a stereolithography composition comprising:
  - a photoinitiator;
  - a monofunctional aryl acrylate monomer, wherein the acrylate group of the monofunctional aryl acrylate monomer is of the formula —O—(C=O)—CH=CH$_2$; and
  - a multifunctional methacrylate or acrylate cross-linker,
  - wherein the monofunctional aryl acrylate monomer is present in the composition in a greater amount than the multifunctional methacrylate or acrylate cross-linker;
- optionally, washing the printed intraocular device; and
- optionally, applying heat and irradiation to fully cure the stereolithography composition.

In another aspect, there is provided a method of producing intraocular devices, the method comprising:
- stereolithographically printing intraocular devices using a stereolithography composition comprising:
  - a photoinitiator;
  - a monofunctional aryl acrylate monomer, wherein the acrylate group of the monofunctional aryl acrylate monomer is of the formula —O—(C=O)—CH=CH$_2$; and
  - a multifunctional methacrylate cross-linker,
  - wherein the monofunctional aryl acrylate monomer is present in the composition in
  - a greater amount than the multifunctional methacrylate cross-linker;
- optionally, washing the printed intraocular device; and
- optionally, applying heat and irradiation to fully cure the stereolithography composition.

In a further aspect, there is provided a stereolithographically printed intraocular device formed by the method described above.

In a further aspect, there is also provided a stereolithography composition, as described herein, having been stereolithographically printed to form an intraocular device, for use in the treatment of cataracts.

In an aspect, there is provided a stereolithographically printed intraocular device for use in the treatment of cataracts. A method of treating cataracts comprising implanting a stereolithographically printed intraocular device into the capsular bag of an eye is also described.

The stereolithography composition described herein has been successfully used to produce intraocular devices, in particular, intraocular lenses that are suitable for implantation as a method of treating, for example, cataracts. In particular, the combination of monofunctional aryl acrylate monomers with multifunctional methacrylate or acrylate cross-linkers has been found to provide the stereolithographically printed intraocular devices with the desired combination of properties for use as intraocular lenses. The monofunctional aryl acrylate monomers provide the printed intraocular devices with the desired optical properties, for example, suitable refractive indices, whilst simultaneously providing the stereolithography composition with sufficient photopolymerisation reactivity for use in stereolithography. The multifunctional methacrylate or acrylate cross-linker ensures that the printed intraocular devices have suitable mechanical properties, in particular, a combination of flexibility, structural integrity and strength. Moreover, by combining monofunctional aryl acrylate monomers with multifunctional methacrylate or acrylate cross-linkers a polymer with suitable mechanical properties may be created. When homopolymerised, acrylate polymers are too soft (having glass transition temperatures that are very low, for example, below 0° C.) whereas methacrylate polymers are too rigid (having glass transition temperatures that are very high). Furthermore, the combined use of these two types of compound also affects the kinetics of the photopolymerisation reaction; whilst acrylates are slow to thermally polymerise, they photopolymerise quickly, enabling the stereolithography composition to solidify on a suitable timescale for stereolithographic printing. In contrast, methacrylates are slow to photopolymerise but quick to thermally polymerise. These differences in reaction kinetics can affect the gradient within the bulk of the polymer, altering the overall physical properties.

Furthermore, the use of stereolithography to produce intraocular devices has been found to avoid or at least mitigate the aforementioned problems of lathing and moulding techniques.

DETAILED DESCRIPTION

Figure 1:
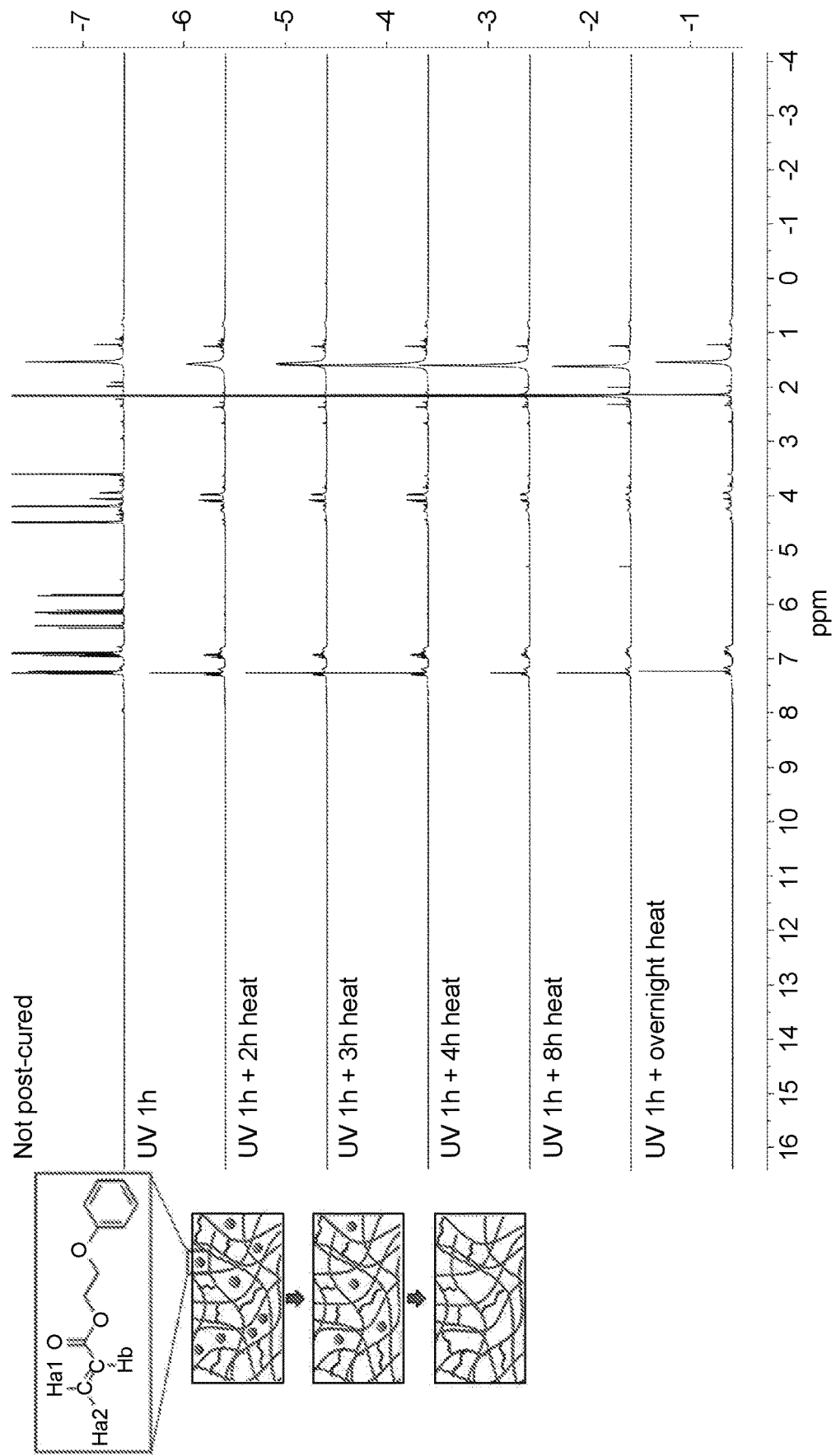
FIG. 1 shows $^1$H NMR spectra obtained to assess the efficacy of post-printing curing of stereolithographically printed intraocular lenses (IOLs).
Figure 2:
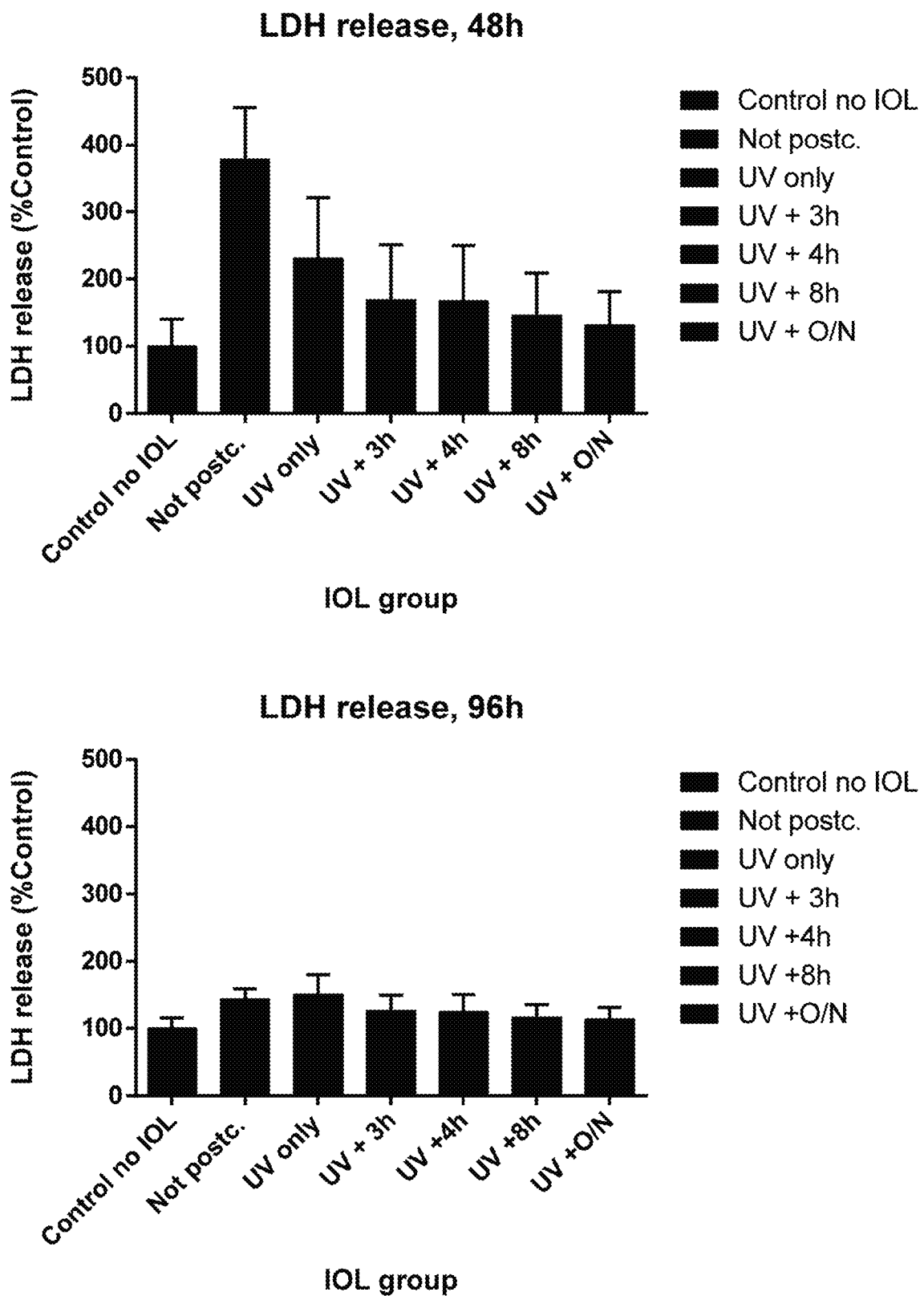
FIG. 2 shows graphs of the results of cytotoxicity evaluation of stereolithographically printed intraocular lenses as shown by LDH release tests after 48 h and 96 h.

It will be readily understood that the components of the present invention, as generally described and illustrated in the figures herein, may be arranged and designed in a wide variety of different configurations. Thus, the descriptions of the embodiments of the present invention, as represented in the figures, is not intended to limit the scope of the invention as claimed, but is merely representative of selected embodiments of the invention.

The features, structures or characteristics of the invention described throughout this specification may be combined in any suitable manner in one or more embodiments. For example, the usage of the phrases "examples", "example embodiments", "some embodiments", "embodiments", or similar language throughout this specification refers to the fact that a particular feature, structure or characteristic described in connection with the embodiment may be included in at least one embodiment of the present invention. Thus, appearances of the phrases "in embodiments", "example embodiments", "in some embodiments", "in other embodiments", or other similar language throughout this specification do not necessarily all refer to the same group of embodiments and the described features, structures, or characteristics may be combined in any suitable manner in one or more embodiments.

Embodiments of the present invention provide the previously mentioned aspects, including optional and preferred features of the various aspects as further described below. Unless otherwise stated, any optional or preferred feature may be combined with any other optional or preferred feature, and with any of the aspects of the invention mentioned herein.

Three-dimensional (3D) printing is any of various processes by which three-dimensional objects may be constructed by formation of one or more layers of solid material from a fluid-like material by combining or fusing adjacent particles or solidifying material.

Stereolithography is a process by which light, which may be produced by a projector or a laser, for example, a UV laser, is focused on a cross-section of a stereolithography composition, that is, a fluid photopolymer resin. The light selectively cures a layer of the resin to form a solid structure. In some examples, a plurality of layers are superimposed on top of one another to form the stereolithographically printed object.

Stereolithography Composition

In an aspect, there is provided a stereolithography composition. The stereolithography composition may comprise a photoinitiator; a monofunctional aryl acrylate monomer, wherein the acrylate group of the monofunctional aryl acrylate monomer is of the formula —O—(C═O)—CH═CH$_2$; and a multifunctional methacrylate or acrylate cross-linker, wherein the monofunctional aryl acrylate monomer is present in the composition in a greater amount than the multifunctional methacrylate or acrylate cross-linker. The stereolithography composition may comprise a photoinitiator; a monofunctional aryl acrylate monomer, wherein the acrylate group of the monofunctional aryl acrylate monomer is of the formula —O—(C═O)—CH═CH$_2$; and a multifunctional methacrylate cross-linker, wherein the monofunctional aryl acrylate monomer is present in the composition in a greater amount than the multifunctional methacrylate cross-linker.

In some examples, when cured, the stereolithography composition has a refractive index of 1.45 to 1.6 as measured by using a refractometry device. An optic for an intraocular lens made from materials having a refractive index below 1.45, in some examples, below 1.5, is necessarily thicker than the ideal to provide the same power as an optic made from a material having a refractive index in the above range. Although intraocular lenses may be made from such materials, they generally require relatively larger incisions for implantation of the intraocular lens.

In some examples, when cured, the stereolithography composition has a glass transition temperature ($T_g$) of less than 37° C. as measured by differential scanning calorimetry (DSC, optionally, on a DSC 2500 from TA instruments), which may be performed by subjecting the cured stereolithography composition to a first heating cycle of from −50° C. to 150° C., followed by a first cooling cycle to −50° C., followed by a second heating cycle to 150° C., with all heating and cooling cycles performed at a heating rate of 10° C./min and the $T_g$ calculated from the DSC thermogram of the second heating cycle as the temperature of the mid-point of the decline in the heat capacity that occurs during this thermal event. In some examples, when cured, the stereolithography composition has a $T_g$ of between about −20° C. and +25° C., in some examples, between about −5° C. and +16° C., in some examples, between 0° C. and +10° C. The $T_g$ of the cured stereolithography composition affects the intraocular device's folding and unfolding characteristics and therefore affects the method of implantation of the intraocular lens. In some examples, the $T_g$ is measured by DSC at 10° C./min, and is determined at the midpoint of the transition of the heat flux curve.

Monofunctional Aryl Acrylate Monomer

The stereolithography composition may comprise a monofunctional aryl acrylate monomer. The monofunctional aryl acrylate monomer may be of the formula —O—(C═O)—CH═CH$_2$. In some examples, the aryl group of the monofunctional aryl acrylate may be directly or indirectly connected to the acrylate group.

As used herein, the term monofunctional may indicate that only one functional group that is photopolymerisable is contained within the monofunctional compound. The photopolymerisable group in the monofunctional aryl acrylate monomer is the acrylate group. Additional functional groups that are not photopolymerisable may be present in the monofunctional compound.

In some examples, the monofunctional aryl acrylate monomer may be a hydrophobic monomer.

As used herein, the term "aryl" may refer to any aromatic group, for example, a group containing a single aromatic ring or multiple aromatic rings that are fused together, directly linked, or indirectly linked (such that the different aromatic rings are bound to a common group such as a methylene or ethylene moiety). Aryl groups described herein may contain, but are not limited to, from 5 to about 50 carbon atoms, or 5 to about 40 carbon atoms, or 5 to about 30 carbon atoms or more.

The ring system of the aryl group may contain one or more heteroatoms, such as oxygen, nitrogen or sulfur. Exemplary aryl groups include phenyl, naphthyl, biphenyl, pyridyl, pyrazinyl, pyrimidinyl, furyl, thiophenyl, pyrrolyl, thiazolyl, pyrazolyl, imidazolyl, 1,2,3-triazolyl, 1,2,4-triazolyl, tetrazolyl, indolyl and purinyl.

The aryl group may be substituted or unsubstituted.

In some examples, the monofunctional aryl acrylate monomer is of the formula R—O—(C═O)—CH═CH$_2$, wherein R is the aryl containing group. In some examples, R is a substituted or unsubstituted aryl group directly connected to —O—(C═O)—CH═CH$_2$. In some examples, R contains a substituted or unsubstituted aryl group indirectly connected to —O—(C═O)—CH═CH$_2$ via, for example, an alkyl chain.

In some examples, R is —(CH$_2$)$_m$YAr, wherein Ar is any aromatic ring which may be substituted or unsubstituted.

In some examples, m is any whole number, including 0. In some examples, m is 0 to 6. In some examples, m is 0, 1, 2, 3, 4, 5 or 6. In some examples, m is 2.

In some examples, Y is nothing or a heteroatom. In some examples, Y is nothing, O, S, NR'. In some examples, R' is selected from H, alkyl, alkoxy, aryl and on/aryl. In some examples, alkyl (and "alk" in alkoxy) is a branched, unbranched, or cyclic saturated hydrocarbon group which may contain from 1 to 10 carbon atoms. In some examples, alkyl is selected from methyl, ethyl, propyl, isopropyl, butyl, isobutyl and tert-butyl. In some examples, alkyl is selected from methyl, ethyl and propyl. In some examples, alkyl is methyl. In some examples, aryl is as defined above.

As used herein, Y is nothing means that instead of Y representing an atom, Y represents a bond, for example, a single bond or a double bond. In some examples, Y represents a single bond such that, for example, —$(CH_2)_m$YAr effectively represents —$(CH_2)_m$Ar.

In some examples, R' is selected from H, $C_nH_{2n+1}$, iso-$OC_3H_7$, $C_6H_5$, or $CH_2C_6H_5$, wherein n may be 1 to 10, in some examples, 1 to 5, in some examples, 1, 2, 3, 4 or 5.

In some examples, Ar is any aryl group as defined above. In some examples, Ar is any aromatic ring which may be substituted with any one or more of $CH_3$, $C_2H_5$, n-$C_3H_7$, iso-$C_3H_7$, $OCh_3$, $C_6H_{11}$, Cl, Br, $C_6H_5$, or $CH_2C_6H_5$. In some examples, Ar is phenyl.

In some examples, R is —$(CH_2)_m$YAr, wherein m is 0 to 6; Y is nothing or a heteroatom; and Ar is any aromatic ring which may be unsubstituted or substituted. In some examples, R is —$(CH_2)_m$YAr, wherein m is 0 to 6; Y is nothing, O, S, NR'; and Ar is any aromatic ring which may be unsubstituted or substituted.

In some examples, R is —$(CH_2)_m$YAr, wherein m is 0 to 6; Y is nothing, O, S, NR', wherein R' is H, $C_nH_{2n+1}$, iso-$OC_3H_7$, $C_6H_5$, or $CH_2C_6H_5$, wherein n may be 1 to 10; and Ar is any aromatic ring which may be unsubstituted or substituted. In some examples, R is —$(CH_2)_m$YAr, wherein m is 0 to 6; Y is nothing, O, S, NR', wherein R' is H, $CH_3$, $C_nH_{2n+1}$, iso-$OC_3H_7$, $C_6H_5$, or $CH_2C_6H_5$, wherein n may be 1 to 10; and Ar is any aromatic ring which may be unsubstituted or substituted with H, $CH_3$, $C_2H_5$, n-$C_3H_7$, iso-$C_3H_7$, $OCh_3$, $C_6H_{11}$, Cl, Br, $C_6H_5$, or $CH_2C_6H_5$.

In some examples, R is —$(CH_2)_m$YAr, wherein m is 0 to 6; Y is nothing, O, S, NR', wherein R' is H, $CH_3$, $C_nH_{2n+1}$, iso-$OC_3H_7$, $C_6H_5$, or $CH_2C_6H_5$, wherein n is 1 to 10; and Ar is any aromatic ring which may be unsubstituted or substituted with H, $CH_3$, $C_2H_5$, n-$C_3H_7$, iso-$C_3H_7$, $OCh_3$, $C_6H_{11}$, Cl, Br, $C_6H_5$, or $CH_2C_6H_5$. In some examples, R is selected from —$(CH_2)_2$Ph and —$(CH_2)_2$OPh. In some examples, R is —$(CH_2)_2$OPh.

In some examples, the monofunctional aryl acrylate monomer constitutes 50 wt. % or more of the stereolithography composition, in some examples, 60 wt. % or more of the stereolithography composition, in some examples, 70 wt. % or more, in some examples, 75 wt. % or more, in some examples, 80 wt. % or more, in some examples, 85 wt. % or more, in some examples, 90 wt. % more, in some examples, 91 wt. % or more, in some examples, 92 wt. % or more, in some examples, 93 wt. % or more, in some examples, 94 wt. % or more, in some examples, 95 wt. % or more, in some examples, 96 wt. % or more, in some examples, 97 wt. % or more, in some examples, 98 wt. % or more, in some examples, 99 wt. % or more of the stereolithography composition. In one example, the monofunctional aryl acrylate monomer constitutes 99 wt. % or less of the stereolithography composition, in some examples, 98 wt. % or less, in some examples, 97 wt. % or less, in some examples, 96 wt. % or less, in some examples, 95 wt. % or less, in some examples, 94 wt. % or less, in some examples, 93 wt. % or less, in some examples, 92 wt. % or less, in some examples, 91 wt. % or less, in some examples, 90 wt. % or less, in some examples, 85 wt. % or less, in some examples, 80 wt. % or less, in some examples, 75 wt. % or less, in some examples, 70 wt. % or less, in some examples, 60 wt. % or less, in some examples, about 50 wt. % or the stereolithography composition. In some examples, the monofunctional aryl acrylate monomer constitutes from about 50 wt. % to about 99 wt. % of the stereolithography composition, in some examples, 60 wt. % to 99 wt. %, in some examples, 70 wt. % to 99 wt. %, in some examples, 75 wt. % to 99 wt. %, in some examples, 80 wt. % to 98 wt. %, in some examples, 85 wt. % to 98 wt. %, in some examples, 90 wt. % to 98 wt. %, in some examples, 91 wt. % to 97 wt. %, in some examples, 91 wt. % to 96 wt. %, in some examples, 92 wt. % to 95 wt. %, in some examples, 93 wt. % to 94 wt. % of the stereolithography composition.

In some examples, the monofunctional aryl acrylate monomer is present in the composition in a greater amount than the multifunctional methacrylate or acrylate cross-linker. In some examples, the ratio (weight to weight) of monofunctional aryl acrylate monomer to multifunctional methacrylate or acrylate cross-linker is from 51:49 to 99:1, in some examples, 55:45 to 98:2, in some examples, 60:40 to 97:3, in some examples, 65:35 to 96:4, in some examples, 70:30 to 95:5, in some examples 75:25 to 97:3, in some examples, 80:20 to 96:4, in some examples, 85:15 to 95:5, in some examples, 90:10 to 94:6, in some examples, 91:9 to 99:2, in some examples, 92:8 to 98:3, in some examples, 93:7 to 94:6.

In some examples, the monofunctional aryl acrylate monomer is present in the composition in a greater amount than the multifunctional methacrylate cross-linker. In some examples, the ratio (weight to weight) of monofunctional aryl acrylate monomer to multifunctional methacrylate cross-linker is from 51:49 to 99:1, in some examples, 55:45 to 98:2, in some examples, 60:40 to 97:3, in some examples, 65:35 to 96:4, in some examples, 70:30 to 95:5, in some examples 75:25 to 97:3, in some examples, 80:20 to 96:4, in some examples, 85:15 to 95:5, in some examples, 90:10 to 94:6, in some examples, 91:9 to 99:2, in some examples, 92:8 to 98:3, in some examples, 93:7 to 94:6.

In some examples, the weight of the multifunctional methacrylate or acrylate cross-linker constitutes 0.5% to 20% of the weight of the monofunctional aryl acrylate monomer, in some examples, 0.5% to 10%, in some examples, 1% to 8%, in some examples, 2% to 7%, in some examples, 3% to 15%, in some examples, 4% to 6%, in some examples, 5% to 8% of the weight of the monofunctional aryl acrylate monomer.

In some examples, the weight of the multifunctional methacrylate cross-linker constitutes 0.5% to 20% of the weight of the monofunctional aryl acrylate monomer, in some examples, 0.5% to 10%, in some examples, 1% to 8%, in some examples, 2% to 7%, in some examples, 3% to 15%, in some examples, 4% to 6%, in some examples, 5% to 8% of the weight of the monofunctional aryl acrylate monomer.

In some examples, the monofunctional aryl acrylate monomer is a mixture of two or more monofunctional aryl acrylate monomers. In some examples, the monofunctional aryl acrylate monomer is a mixture of two or more monofunctional aryl acrylate monomers in which the aryl group is different. In some examples, the monofunctional aryl acrylate monomer is a single monofunctional aryl acrylate monomer.

Multifunctional Methacrylate or Acrylate Cross-Linker

The stereolithography composition may comprise a multifunctional methacrylate or acrylate cross-linker. The stereolithography composition may comprise a multifunctional methacrylate cross-linker. The stereolithography composition may comprise a multifunctional acrylate cross-linker (i.e, in a multifunctional acrylate cross-linker, the acrylate group(s) being of the formula —O—(C=O)—CH=CH$_2$).

As used herein, the term multifunctional indicates that two or more functional groups that are photopolymerisable are contained within the multifunctional compound. At least one of the two or more photopolymerisable functional groups in the multifunctional methacrylate or acrylate cross-linker is a methacrylate group or an acrylate group. In some examples, all of the photopolymerisable functional groups in the multifunctional methacrylate or acrylate cross-linker are methacrylate groups or acrylate groups. At least one of the two or more photopolymerisable functional groups in the multifunctional methacrylate cross-linker is a methacrylate group. In some examples, all of the photopolymerisable functional groups in the multifunctional methacrylate cross-linker are methacrylate groups. At least one of the two or more photopolymerisable functional groups in the multifunctional acrylate cross-linker is an acrylate group. In some examples, all of the photopolymerisable functional groups in the multifunctional acrylate cross-linker are acrylate groups. Additional functional groups that are not photopolymerisable may be present in the multifunctional compound.

The multifunctional methacrylate cross-linker may contain one or more methacrylate groups and one or more other photopolymerisable groups, for example, an acrylate group. The multifunctional methacrylate cross-linker may contain two or more methacrylate groups. In some examples, the multifunctional methacrylate cross-linker contains 2 to 5 methacrylate groups. In some examples, the multifunctional methacrylate cross-linker is selected from dimethacrylate cross-linkers, trimethacrylate cross-linkers, tetramethacrylate cross-linkers and pentamethacrylate cross-linkers. In some examples, the multifunctional methacrylate cross-linker is selected from dimethacrylate cross-linkers and trimethacrylate cross-linkers. In some examples, the multifunctional methacrylate cross-linker is a dimethacrylate cross-linker.

The multifunctional methacrylate or acrylate cross-linker may contain one or more methacrylate groups and one or more acrylate groups. The multifunctional methacrylate or acrylate cross-linker may contain one or more methacrylate groups, one or more acrylate groups and one or more other photopolymerisable groups. In some examples, the multifunctional methacrylate or acrylate cross-linker may contain two or more methacrylate groups and one or more acrylate groups. In some examples, the multifunctional methacrylate or acrylate cross-linker may contain one or more methacrylate groups and two or more acrylate groups. In some examples, the multifunctional methacrylate or acrylate cross-linker may contain 1 to 5 methacrylate groups and 1 to 5 acrylate groups.

The multifunctional acrylate cross-linker may contain one or more acrylate groups and one or more other photopolymerisable groups, for example, a methacrylate group. The multifunctional acrylate cross-linker may contain two or more acrylate groups. In some examples, the multifunctional acrylate cross-linker contains 2 to 5 acrylate groups. In some examples, the multifunctional acrylate cross-linker is selected from diacrylate cross-linkers, triacrylate cross-linkers, tetraacrylate cross-linkers and pentaacrylate cross-linkers. In some examples, the multifunctional acrylate cross-linker is selected from diacrylate cross-linkers and triacrylate cross-linkers. In some examples, the multifunctional acrylate cross-linker is a diacrylate cross-linker.

In some examples, the multifunctional methacrylate cross-linker is a hydrophilic multifunctional methacrylate cross-linker. In some examples, the multifunctional acrylate cross-linker is a hydrophilic multifunctional acrylate cross-linker.

In some examples, the dimethacrylate cross-linker is of the formula CH$_2$=CHMe-(C=O)—O—R"—O—(C=O)—CHMe=CH$_2$. In some examples, R" is selected from alkyl, alkyl-O-alkyl, polyalkyl and polyether. In some examples, R" is selected from alkyl, polyalkyl and polyether. In some examples, R" is selected from unbranched alkyl, polyethylene and unbranched polyether. In some examples, R" is polyether, for example, unbranched polyether. When R" is polyether, the oxygen groups in —O—R"—O— of the formula above are oxygen groups of the polyether such that no oxygen to oxygen bonds are present in the dimethacrylate cross-linker.

In some examples, R" is alkyl, wherein alkyl is selected from branched, unbranched, or cyclic saturated hydrocarbon groups which may contain from 1 to 10 carbon atoms. In some examples, alkyl is selected from methyl, ethyl, propyl, isopropyl, butyl, isobutyl and tert-butyl. In some examples, alkyl is selected from methyl, ethyl and propyl. In some examples, alkyl is methyl.

In some examples, R" is polyether, wherein polyether is selected from branched, unbranched, or cyclic saturated polyether groups. In some examples, polyether is selected from poly(formaldehyde), poly(ethylene glycol), poly(propylene glycol), poly(1,3-propanediol), poly(1,2-butanediol), poly(1,3-butanediol), poly(1,4-butanediol), poly(1,5-pentanediol), poly(1,6-hexanediol). In some examples, the polyether is poly(ethylene glycol).

In some examples, the dimethacrylate cross-linker is ethylene glycol dimethacrylate, diethylene glycol dimethacrylate, 1,3-propanediol di methacrylate, 1,4-butanediol dimethacrylate, 1,5-pentanediol dimethacrylate, 1,6-hexanediol dimethacrylate. In some examples, the dimethacrylate cross-linker is poly(formaldehyde) dimethacrylate, poly(ethylene glycol) dimethacrylate, poly(propylene glycol) dimethacrylate, poly(1,3-propanediol) dimethacrylate, poly(1,2-butanediol) dimethacrylate, poly(1,3-butanediol) dimethacrylate, poly(1,4-butanediol) dimethacrylate, poly(1,5-pentanediol) dimethacrylate, poly(1,6-hexanediol) dimethacrylate. In some examples, the dimethacrylate cross-linker is poly(ethylene glycol) dimethacrylate.

In some examples, the diacrylate cross-linker is of the formula CH$_2$=CH$_2$—(C=O)—O—R"—O—(C=O)—CH$_2$=CH$_2$. In some examples, R" is as defined for the dimethacrylate cross-linker.

In some examples, the diacrylate cross-linker is ethylene glycol diacrylate, diethylene glycol diacrylate, 1,3-propanediol diacrylate, 1,4-butanediol diacrylate, 1,5-pentanediol diacrylate, 1,6-hexanediol diacrylate. In some examples, the diacrylate cross-linker is poly(formaldehyde) diacrylate, poly(ethylene glycol) diacrylate, poly(propylene glycol) diacrylate, poly(1,3-propanediol) diacrylate, poly(1,2-butanediol) diacrylate, poly(1,3-butanediol) diacrylate, poly(1,4-butanediol) diacrylate, poly(1,5-pentanediol) diacrylate, poly(1,6-hexanediol) diacrylate. In some examples, the diacrylate cross-linker is poly(ethylene glycol) diacrylate.

In some examples, the multifunctional methacrylate cross-linker has a number average molecular weight of 500 or more, in some examples, 550 or more, in some examples, 600 or more, in some examples, 650 or more, in some The multifunctional methacrylate or acrylate cross-linker is selected from diacrylate cross-linkers and triacrylate cross-linkers. In some examples, the multifunctional acrylate cross-linker is a diacrylate cross-linker.

examples, 700 or more, in some examples, 750 or more, in some examples, 800 or more, in some examples, 850 or more, in some examples, 900 or more, in some examples, 1000 or more, in some examples, 1100 or more, in some examples, 1200 or more, in some examples, 1300 or more, in some examples, 1400 or more, in some examples 1500 or more, in some examples, 1600 or more, in some examples, 1700 or more, in some examples, 1800 or more, in some examples, 1900 or more, in some examples, 2000 or more, in some examples, 2100 or more, in some examples, 2200 or more, in some examples 2300 or more, in some examples, 2500 or more. In some examples, the multifunctional methacrylate cross-linker has a number average molecular weight of 2500 or less, in some examples, 2400 or less, in some examples, 2300 or less, in some examples, 2200 or less, in some examples, 2100 or less, in some examples, 2000 or less, in some examples, 1900 or less, in some examples, 1800 or less, in some examples, 1700 or less, in some examples, 1600 or less, in some examples, 1500 or less, in some examples, 1400 or less, in some examples, 1300 or less, in some examples, 1200 or less, in some examples, 1100 or less, in some examples, 1000 or less, in some examples, 950 or less, in some examples, 900 or less, in some examples, 850 or less, in some examples, 800 or less, in some examples, 750 or less, in some examples, 700 or less, in some examples, 650 or less, in some examples, 600 or less, in some examples, 550 or less, in some examples, about 500. In some examples, the multifunctional methacrylate cross-linker has a number average molecular weight of 500 to 2000, in some examples, 550 to 1500, in some examples, 600 to 1000, in some examples, 650 to 900, in some examples, 700 to 950, in some examples, 750 to 800.

In some examples, the multifunctional acrylate cross-linker has a number average molecular weight of 500 or more, in some examples, 550 or more, in some examples, 600 or more, in some examples, 650 or more, in some examples, 700 or more, in some examples, 750 or more, in some examples, 800 or more, in some examples, 850 or more, in some examples, 900 or more, in some examples, 1000 or more, in some examples, 1100 or more, in some examples, 1200 or more, in some examples, 1300 or more, in some examples, 1400 or more, in some examples 1500 or more, in some examples, 1600 or more, in some examples, 1700 or more, in some examples, 1800 or more, in some examples, 1900 or more, in some examples, 2000 or more, in some examples, 2100 or more, in some examples, 2200 or more, in some examples 2300 or more, in some examples, 2500 or more. In some examples, the multifunctional acrylate cross-linker has a number average molecular weight of 2500 or less, in some examples, 2400 or less, in some examples, 2300 or less, in some examples, 2200 or less, in some examples, 2100 or less, in some examples, 2000 or less, in some examples, 1900 or less, in some examples, 1800 or less, in some examples, 1700 or less, in some examples, 1600 or less, in some examples, 1500 or less, in some examples, 1400 or less, in some examples, 1300 or less, in some examples, 1200 or less, in some examples, 1100 or less, in some examples, 1000 or less, in some examples, 950 or less, in some examples, 900 or less, in some examples, 850 or less, in some examples, 800 or less, in some examples, 750 or less, in some examples, 700 or less, in some examples, 650 or less, in some examples, 600 or less, in some examples, 550 or less, in some examples, about 500. In some examples, the multifunctional acrylate cross-linker has a number average molecular weight of 500 to 2000, in some examples, 550 to 1500, in some examples, 600 to 1000, in some examples, 650 to 900, in some examples, 700 to 950, in some examples, 750 to 800.

In some examples, the multifunctional methacrylate cross-linker constitutes 25 wt. % or less of the stereolithography composition, in some examples, 20 wt. % or less, in some examples, 15 wt. % or less, in some examples, 10 wt. % or less, in some examples, 9.5 wt. % or less, in some examples, 9 wt. % or less, in some examples, 8.5 wt. % or less, in some examples, 8 wt. % or less, in some examples, 7.5 wt. % or less, in some examples, 7 wt. % or less, in some examples, 6.5 wt. % or less, in some examples, 6 wt. % or less, in some examples, 5.5 wt. % or less, in some examples, 5 wt. % or less, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.5 wt. % or less of the stereolithography composition. In some examples, the multifunctional methacrylate cross-linker constitutes 0.5 wt. % or more of the stereolithography composition, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more, in some examples, 5.5 wt. % or more, in some examples, 6 wt. % or more, in some examples, 6.5 wt. % or more, in some examples, 7 wt. % or more, in some examples, 7.5 wt. % or more, in some examples, 8 wt. % or more, in some examples, 8.5 wt. % or more, in some examples, 9 wt. % or more, in some examples, 9.5 wt. % or more, in some examples, 10 wt. % or more, in some examples, 15 wt. % or more, in some examples, 20 wt. % or more, in some examples, 25 wt. % or more of the stereolithography composition. In some examples, the multifunctional methacrylate cross-linker constitutes 0.5 wt. % to 25 wt. % of the stereolithography composition, in some examples, 1.5 wt. % to 20 wt. %, in some examples, 2 wt. % to 15 wt. %, in some examples, 2.5 wt. % to 10 wt. %, in some examples, 3 wt. % to 9.5 wt. %, in some examples, 3.5 wt. % to 9 wt. %, in some examples, 4 wt. % to 8.5 wt. %, in some examples, 4.5 wt. % to 8 wt. %, in some examples, 5 wt. % to 7.5 wt. %, in some examples, 5.5 wt. % to 7 wt. %, in some examples, 6 wt. % to 7.5 wt. %, in some examples, 6.5 wt. % to 7 wt. % of the stereolithography composition.

In some examples, the multifunctional acrylate cross-linker constitutes 25 wt. % or less of the stereolithography composition, in some examples, 20 wt. % or less, in some examples, 15 wt. % or less, in some examples, 10 wt. % or less, in some examples, 9.5 wt. % or less, in some examples, 9 wt. % or less, in some examples, 8.5 wt. % or less, in some examples, 8 wt. % or less, in some examples, 7.5 wt. % or less, in some examples, 7 wt. % or less, in some examples, 6.5 wt. % or less, in some examples, 6 wt. % or less, in some examples, 5.5 wt. % or less, in some examples, 5 wt. % or less, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.5 wt. % or less of the stereolithography composition. In some examples, the multifunctional acrylate cross-linker constitutes 0.5 wt. % or more of the stereolithography composition, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more, in some examples, 5.5 wt. % or more, in some examples, 6 wt. % or more, in some examples, 6.5 wt. % or more, in some examples, 7 wt. % or more, in some examples, 7.5 wt. % or more, in some examples, 8 wt. % or more, in some examples, 8.5 wt. % or more, in some examples, 9 wt. % or more, in some examples, 9.5 wt. % or more, in some examples, 10 wt. % or more, in some examples, 15 wt. % or more, in some examples, 20 wt. % or more, in some examples, 25 wt. % or more of the stereolithography composition. In some examples, the multifunctional acrylate cross-linker constitutes 0.5 wt. % to 25 wt. % of the stereolithography composition, in some examples, 1.5 wt. % to 20 wt. %, in some examples, 2 wt. % to 15 wt. %, in some examples, 2.5 wt. % to 10 wt. %, in some examples, 3 wt. % to 9.5 wt. %, in some examples, 3.5 wt. % to 9 wt. %, in some examples, 4 wt. % to 8.5 wt. %, in some examples, 4.5 wt. % to 8 wt. %, in some examples, 5 wt. % to 7.5 wt. %, in some examples, 5.5 wt. % to 7 wt. %, in some examples, 6 wt. % to 7.5 wt. %, in some examples, 6.5 wt. % to 7 wt. % of the stereolithography composition.

In some examples, the multifunctional methacrylate cross-linker is a dimethacrylate cross-linker and constitutes 25 wt. % or less of the stereolithography composition, in some examples, 20 wt. % or less, in some examples, 15 wt. % or less, in some examples, 10 wt. % or less, in some examples, 9.5 wt. % or less, in some examples, 9 wt. % or less, in some examples, 8.5 wt. % or less, in some examples, 8 wt. % or less, in some examples, 7.5 wt. % or less, in some examples, 7 wt. % or less, in some examples, 6.5 wt. % or less, in some examples, 6 wt. % or less, in some examples, 5.5 wt. % or less, in some examples, 5 wt. % or less, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.5 wt. % or less of the stereolithography composition In some examples, the multifunctional methacrylate cross-linker is a dimethacrylate cross-linker and constitutes 0.5 wt. % or more of the stereolithography composition, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more, in some examples, 5.5 wt. % or more, in some examples, 6 wt. % or more, in some examples, 6.5 wt. % or more, in some examples, 7 wt. % or more, in some examples, 7.5 wt. % or more, in some examples, 8 wt. % or more, in some examples, 8.5 wt. % or more, in some examples, 9 wt. % or more, in some examples, 9.5 wt. % or more, in some examples, 10 wt. % or more, in some examples, 15 wt. % or more, in some examples, 20 wt. % or more, in some examples, 25 wt. % or more of the stereolithography composition. In some examples, the multifunctional methacrylate cross-linker is a dimethacrylate cross-linker and constitutes 0.5 wt. % to 25 wt. % of the stereolithography composition, in some examples, 1.5 wt. % to 20 wt. %, in some examples, 2 wt. % to 15 wt. %, in some examples, 2.5 wt. % to 10 wt. %, in some examples, 3 wt. % to 9.5 wt. %, in some examples, 3.5 wt. % to 9 wt. %, in some examples, 4 wt. % to 8.5 wt. %, in some examples, 4.5 wt. % to 8 wt. %, in some examples, 5 wt. % to 7.5 wt. %, in some examples, 5.5 wt. % to 7 wt. %, in some examples, 6 wt. % to 7.5 wt. %, in some examples, 6.5 wt. % to 7 wt. % of the stereolithography composition.

In some examples, the multifunctional acrylate cross-linker is a diacrylate cross-linker and constitutes 25 wt. % or less of the stereolithography composition, in some examples, 20 wt. % or less, in some examples, 15 wt. % or less, in some examples, 10 wt. % or less, in some examples, 9.5 wt. % or less, in some examples, 9 wt. % or less, in some examples, 8.5 wt. % or less, in some examples, 8 wt. % or less, in some examples, 7.5 wt. % or less, in some examples, 7 wt. % or less, in some examples, 6.5 wt. % or less, in some examples, 6 wt. % or less, in some examples, 5.5 wt. % or less, in some examples, 5 wt. % or less, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.5 wt. % or less of the stereolithography composition In some examples, the multifunctional acrylate cross-linker is a diacrylate cross-linker and constitutes 0.5 wt. % or more of the stereolithography composition, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more, in some examples, 5.5 wt. % or more, in some examples, 6 wt. % or more, in some examples, 6.5 wt. % or more, in some examples, 7 wt. % or more, in some examples, 7.5 wt. % or more, in some examples, 8 wt. % or more, in some examples, 8.5 wt. % or more, in some examples, 9 wt. % or more, in some examples, 9.5 wt. % or more, in some examples, 10 wt. % or more, in some examples, 15 wt. % or more, in some examples, 20 wt. % or more, in some examples, 25 wt. % or more of the stereolithography composition. In some examples, the multifunctional acrylate cross-linker is a diacrylate cross-linker and constitutes 0.5 wt. % to 25 wt. % of the stereolithography composition, in some examples, 1.5 wt. % to 20 wt. %, in some examples, 2 wt. % to 15 wt. %, in some examples, 2.5 wt. % to 10 wt. %, in some examples, 3 wt. % to 9.5 wt. %, in some examples, 3.5 wt. % to 9 wt. %, in some examples, 4 wt. % to 8.5 wt. %, in some examples, 4.5 wt. % to 8 wt. %, in some examples, 5 wt. % to 7.5 wt. %, in some examples, 5.5 wt. % to 7 wt. %, in some examples, 6 wt. % to 7.5 wt. %, in some examples, 6.5 wt. % to 7 wt. % of the stereolithography composition.

In some examples, the multifunctional methacrylate cross-linker is a trimethacrylate and constitutes 10 wt. % or less of the stereolithography composition, in some examples, 9.5 wt. % or less, in some examples, 9 wt. % or less, in some examples, 8.5 wt. % or less, in some examples, 8 wt. % or less, in some examples, 7.5 wt. % or less, in some examples, 7 wt. % or less, in some examples, 6.5 wt. % or less, in some examples, 6 wt. % or less, in some examples, 5.5 wt. % or less, in some examples, 5 wt. % or less, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.5 wt. % or less of the stereolithography composition. In some examples, the multifunctional methacrylate cross-linker is a trimethacrylate and constitutes 0.5 wt. % or more of the stereolithography composition, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more, in some examples, 5.5 wt. % or more, in some examples, 6 wt. % or more, in some examples, 6.5 wt. % or more, in some examples, 7 wt. % or more, in some examples, 7.5 wt. % or more, in some examples, 8 wt. % or more, in some examples, 8.5 wt. % or more, in some examples, 9 wt. % or more, in some examples, 9.5 wt. % or more, in some examples, 10 wt. % or more of the stereolithography composition. In some examples, the multifunctional methacrylate cross-linker is a trimethacrylate cross-linker and constitutes 0.5 wt. % to 10 wt. % of the stereolithography composition, in some examples, 1.5 wt. % to 9.5 wt. %, in some examples, 2 wt. % to 9 wt. %, in some examples, 2.5 wt. % to 8.5 wt. %, in some examples, 3 wt. % to 7 wt. %, in some examples, 3.5 wt. % to 7.5 wt. %, in some examples, 4 wt. % to 6 wt. %, in some examples, 4.5 wt. % to 6.5 wt. %, in some examples, 5 wt. % to 6.5 wt. % of the stereolithography composition.

In some examples, the multifunctional acrylate cross-linker is a triacrylate and constitutes 10 wt. % or less of the stereolithography composition, in some examples, 9.5 wt. % or less, in some examples, 9 wt. % or less, in some examples, 8.5 wt. % or less, in some examples, 8 wt. % or less, in some examples, 7.5 wt. % or less, in some examples, 7 wt. % or less, in some examples, 6.5 wt. % or less, in some examples, 6 wt. % or less, in some examples, 5.5 wt. % or less, in some examples, 5 wt. % or less, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or more, in some examples, 0.5 wt. % or less of the stereolithography composition. In some examples, the multifunctional acrylate cross-linker is a triacrylate and constitutes 0.5 wt. % or more of the stereolithography composition, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more, in some examples, 5.5 wt. % or more, in some examples, 6 wt. % or more, in some examples, 6.5 wt. % or more, in some examples, 7 wt. % or more, in some examples, 7.5 wt. % or more, in some examples, 8 wt. % or more, in some examples, 8.5 wt. % or more, in some examples, 9 wt. % or more, in some examples, 9.5 wt. % or more, in some examples, 10 wt. % or more of the stereolithography composition. In some examples, the multifunctional acrylate cross-linker is a triacrylate cross-linker and constitutes 0.5 wt. % to 10 wt. % of the stereolithography composition, in some examples, 1.5 wt. % to 9.5 wt. %, in some examples, 2 wt. % to 9 wt. %, in some examples, 2.5 wt. % to 8.5 wt. %, in some examples, 3 wt. % to 7 wt. %, in some examples, 3.5 wt. % to 7.5 wt. %, in some examples, 4 wt. % to 6 wt. %, in some examples, 4.5 wt. % to 6.5 wt. %, in some examples, 5 wt. % to 6.5 wt. % of the stereolithography composition.

In some examples, the multifunctional methacrylate cross-linker is a tetramethacrylate cross-linker and constitutes 5 wt. % or less of the stereolithography composition, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.9 wt. % or less, in some examples, 0.8 wt. % or less, in some examples, 0.7 wt. % or less, in some examples, 0.6 wt. % or less, in some examples, 0.5 wt. % or less, in some examples, 0.4 wt. % or less, in some examples, 0.3 wt. % or less, in some examples, 0.2 wt. % or less, in some examples, 0.1 wt. % or less of the stereolithography composition. In some examples, the multifunctional methacrylate cross-linker constitutes 0.1 wt. % or more of the stereolithography composition, in some examples, 0.2 wt. % or more, in some examples, 0.3 wt. % or more, in some examples, 0.4 wt. % or more, in some examples, 0.5 wt. % or more, in some examples, 0.6 wt. % or more, in some examples, 0.7 wt. % or more, in some examples, 0.8 wt. % or more, in some examples, 0.9 wt. % or more, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more of the stereolithography composition. In some examples, the multifunctional methacrylate cross-linker constitutes 0.1 wt. % to 5 wt. % of the stereolithography composition, in some examples, 0.2 wt. % to 4.5 wt. %, in some examples, 0.3 wt. % to 4 wt. %, in some examples, 0.4 wt. % to 3.5 wt. %, in some examples, 0.5 wt. % to 3 wt. %, in some examples, 0.6 wt. % to 2.5 wt. %, in some examples, 0.7 wt. % to 2 wt. %, in some examples, 0.8 wt. % to 1.5 wt. %, in some examples, 0.9 wt. % to 1 wt. % of the stereolithography composition.

In some examples, the multifunctional acrylate cross-linker is a tetraacrylate cross-linker and constitutes 5 wt. % or less of the stereolithography composition, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.9 wt. % or less, in some examples, 0.8 wt. % or less, in some examples, 0.7 wt. % or less, in some examples, 0.6 wt. % or less, in some examples, 0.5 wt. % or less, in some examples, 0.4 wt. % or less, in some examples, 0.3 wt. % or less, in some examples, 0.2 wt. % or less, in some examples, 0.1 wt. % or less of the stereolithography composition. In some examples, the multifunctional acrylate cross-linker constitutes 0.1 wt. % or more of the stereolithography composition, in some examples, 0.2 wt. % or more, in some examples, 0.3 wt. % or more, in some examples, 0.4 wt. % or more, in some examples, 0.5 wt. % or more, in some examples, 0.6 wt. % or more, in some examples, 0.7 wt. % or more, in some examples, 0.8 wt. % or more, in some examples, 0.9 wt. % or more, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more of the stereolithography composition. In some examples, the multifunctional acrylate cross-linker constitutes 0.1 wt. % to 5 wt. % of the stereolithography composition, in some examples, 0.2 wt. % to 4.5 wt. %, in some examples, 0.3 wt. % to 4 wt. %, in some examples, 0.4 wt. % to 3.5 wt. %, in some examples, 0.5 wt.

% to 3 wt. %, in some examples, 0.6 wt. % to 2.5 wt. %, in some examples, 0.7 wt. % to 2 wt. %, in some examples, 0.8 wt. % to 1.5 wt. %, in some examples, 0.9 wt. % to 1 wt. % of the stereolithography composition.

In some examples, the multifunctional methacrylate or acrylate cross-linker is a mixture of two or more multifunctional methacrylate or acrylate cross-linkers. In some examples, the multifunctional methacrylate or acrylate cross-linker is a mixture of a single multifunctional methacrylate cross-linker and a single multifunctional acrylate.

In some examples, the multifunctional methacrylate cross-linker is a mixture of two or more multifunctional methacrylate cross-linkers. In some examples, the multifunctional methacrylate cross-linker is a single multifunctional methacrylate cross-linker.

In some examples, the multifunctional acrylate cross-linker is a mixture of two or more multifunctional acrylate cross-linkers. In some examples, the multifunctional acrylate cross-linker is a single multifunctional acrylate cross-linker.

Photoinitiator

The stereolithography composition may comprise a photoinitiator. As used herein, the term "photoinitiator" refers to a substance capable of generating radicals upon receiving light. Therefore, radicals are generated by irradiation of light thereby inducing radical polymerization. The light may be UV light. The radical polymerization reaction may be a polymerization method of forming a polymer by successive addition of free radicals, in which the radicals may be commonly formed via a number of different mechanisms usually involving separate initiator molecules.

In some examples, the photoinitiator may be a mixture of photoinitiators.

The photoinitiator may be selected from diphenyl(2,4,6-trimethylbenzoyl)phosphine oxide (TPO), an acetophenone derivative (such as dimethoxyphenylacetophenone), benzophenone, phenylbis(2,4,6-trimethylbenzoyl)phosphine oxide (BAPO), and 2-(4-methoxystyryl)-4,6-bis(trichloromethyl)-1,3,5-triazine. In some examples, the photoinitiator may be TPO.

In some examples, the photoinitiator constitutes 5 wt. % or less of the stereolithography composition, in some examples, 4.5 wt. % or less, in some examples, 4 wt. % or less, in some examples, 3.5 wt. % or less, in some examples, 3 wt. % or less, in some examples, 2.5 wt. % or less, in some examples, 2 wt. % or less, in some examples, 1.5 wt. % or less, in some examples, 1 wt. % or less, in some examples, 0.9 wt. % or less, in some examples, 0.8 wt. % or less, in some examples, 0.7 wt. % or less, in some examples, 0.6 wt. % or less, in some examples, 0.5 wt. % or less, in some examples, 0.4 wt. % or less, in some examples, 0.3 wt. % or less, in some examples, 0.2 wt. % or less, in some examples, 0.1 wt. % or less, in some examples, 0.05 wt. % or less, in some examples, 0.01 wt. % or less of the stereolithography composition. In some examples, the photoinitiator constitutes 0.01 wt. % or more of the stereolithography composition, in some examples, 0.05 wt. % or more, in some examples, 0.1 wt. % or more, in some examples, 0.2 wt. % or more, in some examples, 0.3 wt. % or more, in some examples, 0.4 wt. % or more, in some examples, 0.5 wt. % or more, in some examples, 0.6 wt. % or more, in some examples, 0.7 wt. % or more, in some examples, 0.8 wt. % or more, in some examples, 0.9 wt. % or more, in some examples, 1 wt. % or more, in some examples, 1.5 wt. % or more, in some examples, 2 wt. % or more, in some examples, 2.5 wt. % or more, in some examples, 3 wt. % or more, in some examples, 3.5 wt. % or more, in some examples, 4 wt. % or more, in some examples, 4.5 wt. % or more, in some examples, 5 wt. % or more of the stereolithography composition. In some examples, the photoinitiator constitutes 0.01 wt. % to 5 wt. % of the stereolithography composition, in some examples, 0.05 wt. % to 4.5 wt. %, in some examples, 0.1 wt. % to 4 wt. %, in some examples, 0.2 wt. % to 3.5 wt. %, in some examples, 0.3 wt. % to 3 wt. %, in some examples, 0.4 wt. % to 2.5 wt. %, in some examples, 0.5 wt. % to 2 wt. %, in some examples, 0.6 wt. % to 1.5 wt. %, in some examples, 0.7 wt. % to 1 wt. %, in some examples, 0.8 wt. % to 1.5 wt. %, in some examples, 0.9 wt. % to 1 wt. % of the stereolithography composition.

Other Additives

In some examples, the stereolithography composition may contain an additive or a plurality of additives. The additive or plurality of additives may include a UV absorber that imparts UV absorption properties to the IOL. The additive or plurality of additives may include additional monomers.

The UV absorber may be selected from 2-(2-hydroxy-5-methylphenyl)benzotriazole and 2,5-bis(5-tert-butyl-benzoxazol-2-yl)thiophene.

In some examples, the additive may be a hydrophilic monofunctional monomer. The hydrophilic monofunctional monomer may be selected from 2-hydroxyethyl acrylate, 2-hydroxyethyl methacrylate, 2-N-ethylacrylate pyrrolidone, 2-hydroxy-3-phenoxypropyl acrylate, 2,3-dihydroxypropyl acrylate, 2,3-dihydroxypropyl methacrylate, 2-N-vinyl pyrrolidone, polyethylene oxide:200 monomethyl ether monomethacrylate, polyethylene oxide:200 monomethacrylate, polyethylene oxide:1000 dimethacrylate.

Method of Producing Intraocular Devices

In an aspect, there is provided a method of producing intraocular devices. The method may comprise stereolithographically printing intraocular devices using a stereolithography composition, which may be as described herein.

In some examples, the method may comprise stereolithographically printing intraocular devices using a stereolithography composition; and washing the printed intraocular device.

In some examples, the method may comprise stereolithographically printing intraocular devices using a stereolithography composition; and applying heat to fully cure the stereolithography composition. In some examples, the method may comprise stereolithographically printing intraocular devices using a stereolithography composition; and applying irradiation to fully cure the stereolithography composition. In some examples, the method may comprise stereolithographically printing intraocular devices using a stereolithography composition; and applying heat and irradiation to fully cure the stereolithography composition.

In some examples, the method may comprise stereolithographically printing intraocular devices using a stereolithography composition; washing the printed intraocular device; and applying heat to fully cure the stereolithography composition. In some examples, the method may comprise stereolithographically printing intraocular devices using a stereolithography composition; washing the printed intraocular device; and applying irradiation to fully cure the stereolithography composition. In some examples, the method may comprise stereolithographically printing intraocular devices using a stereolithography composition; washing the printed intraocular device; and applying heat and irradiation to fully cure the stereolithography composition.

The stereolithography composition may be the stereolithography composition described above. In some examples, the method may comprise stereolithographically printing intraocular devices using a stereolithography composition; washing the printed intraocular device; and applying heat and irradiation to fully cure the stereolithography composition, wherein the stereolithography composition comprises a photoinitiator; a monofunctional aryl acrylate monomer; and a multifunctional methacrylate or acrylate cross-linker, wherein the monofunctional aryl acrylate monomer is present in the composition in a greater amount than the multifunctional methacrylate or acrylate cross-linker. In some examples, the method may comprise stereolithographically printing intraocular devices using a stereolithography composition; washing the printed intraocular device; and applying heat and irradiation to fully cure the stereolithography composition, wherein the stereolithography composition comprises a photoinitiator; a monofunctional aryl acrylate monomer; and a multifunctional methacrylate cross-linker, wherein the monofunctional aryl acrylate monomer is present in the composition in a greater amount than the multifunctional methacrylate cross-linker.

In some examples, a stereolithography apparatus is used to stereolithographically print intraocular devices using a stereolithography composition. In some examples, a stereolithography apparatus includes a vat and an elevator platform, which is lifted and lowered into the vat. The vat is filled with the stereolithography composition.

In some examples, the stereolithography apparatus is a laser-based stereolithography apparatus or a digital light processing (DLP) stereolithography apparatus.

During stereolithographic printing, a light source, for example, a laser or a projector, selectively initiates photopolymerisation in a layer of the stereolithography composition.

Successive layers of stereolithography composition may be selectively cured using the light source to create the intraocular device. In some examples, the light source is a laser, optionally a UV laser. In some examples, the light source is selected such that it emits a wavelength corresponding to the wavelength required by the photoinitiator used in the stereolithography composition to initiate the photopolymerisation. In some examples, the photoinitiator is selected such that the excitation wavelength of the photoinitiator is comparable to the wavelength emitted by the light source. In some examples, the photoinitiator is selected such that the excitation wavelength of the photoinitiator is within the range of wavelengths emitted by the light source.

In laser-based stereolithographic printing, the laser moves across the layer of the stereolithography composition to selectively initiate photopolymerisation and therefore selectively solidify the layer of stereolithography composition in the shape required for the particular layer of the device being printed, that is, the intraocular device. In DLP stereolithographic printing, a projector projects an image of the entire layer of the device being printed, that is, the intraocular device, onto the stereolithography composition to selectively initiate photopolymerisation and therefore, selectively solidify the layer of the stereolithography composition in the shape required for the particular layer of the device being printed.

In some examples, the intraocular device is stereolithographically printed using inverted stereolithography. In an inverted stereolithography apparatus, the vat has a base that is transparent to light from the light source and light is shone up into the vat to cure the stereolithography composition. Inverted stereolithography may involve lowering the elevator platform into the vat containing the stereolithography composition until only a thin layer (e.g. of a desired thickness of the layer—see paragraph below) of the stereolithography composition remains between the lower surface of the elevator platform and the transparent base of the vat. The light is then selectively shone through the transparent base to selectively cure the stereolithography composition. The elevator platform and the cured layer of stereolithography composition may then be raised from the transparent base of the vat allowing stereolithography composition to flow between the cured layer of stereolithography composition and the transparent base of the vat. The light may then be shone through the transparent base to selectively cure the next layer of stereolithography composition (which again may be of a desired thickness—see paragraph below). These steps may be repeated to build the intraocular device layer-by-layer.

In some examples, the intraocular device is stereolithographically printed using a process similar to the one described in the previous paragraph except instead of the light source being directed at the vat of stereolithography composition from below, the light is directed at the vat from above and the elevator platform starts near the surface of stereolithography composition, with a layer of uncured stereolithography composition above the platform (this layer being of a desired thickness of the layer to be formed—see paragraph below for suitable thicknesses) and, to cure the layer, and the elevator platform is then lowered into the vat of stereolithography composition rather than being raised out of the vat, following formation of each layer.

In some examples, stereolithographically printing the intraocular device comprises curing one or more layers of stereolithography composition. In some examples, stereolithographically printing the intraocular device comprises successively curing multiple layers of stereolithography composition. In some examples, each cured layer of stereolithography composition has a thickness of 0.025 mm or more, in some examples, 0.03 mm or more, in some examples, 0.04 mm or more, in some examples, 0.05 mm or more, in some examples, 0.06 mm or more, in some examples, 0.07 mm or more, in some examples, 0.08 mm or more, in some examples, 0.09 mm or more, in some examples, 0.1 mm or more, in some examples, 0.15 mm or more, in some examples, 0.2 mm or more, in some examples, 0.25 mm or more, in some examples, 0.3 mm or more, in some examples, 0.35 mm or more, in some examples, 0.4 mm or more, in some examples, 0.45 mm or more, in some examples, 0.5 mm or more, in some examples, 0.55 mm or more, in some examples, 0.6 mm or more, in some examples, 0.65 mm or more, in some examples, 0.7 mm or more, in some examples, 0.75 mm or more, in some examples, 0.8 mm or more, in some examples, 0.85 mm or more, in some examples, 0.9 mm or more, in some examples, 0.95 mm or more, in some examples, 1 mm or more. In some examples, each cured layer of stereolithography composition has a thickness of 1 mm or less, in some examples, 0.95 mm or less, in some examples, 0.9 mm or less, in some examples, 0.85 mm or less, in some examples, 0.8 mm or less, in some examples, 0.75 mm or less, in some examples, 0.7 mm or less, in some examples, 0.65 mm or less, in some examples, 0.6 mm or less, in some examples, 0.55 mm or less, in some examples, 0.5 mm or less, in some examples, 0.45 mm or less, in some examples, 0.4 mm or less, in some examples, 0.35 mm or less, in some examples, 0.3 mm or less, in some examples, 0.25 mm or less, in some examples, 0.2 mm or less, in some examples, 0.1 mm or less, in some examples, 0.09 mm or less, in some examples, 0.08 mm or less, in some examples, 0.07 mm or less, in some examples, 0.06 mm or less, in some examples, 0.05 mm or less, in some examples, 0.04 mm or less, in some examples, 0.03 mm or less, in some examples, about 0.025 mm or less. In some examples, each cured layer of stereolithography composition may have a thickness of 0.025 mm to 1 mm, in some examples, 0.025 mm to 0.95 mm, in some examples, 0.03 mm to 0.9 mm, in some examples, 0.04 mm to 0.85 mm, in some examples, 0.05 mm to 0.8 mm, in some examples, 0.08 mm to 0.75 mm, in some examples, 0.09 mm to 0.7 mm, in some examples, 0.1 mm to 0.65 mm, in some examples, 0.2 mm to 0.6 mm, in some examples, 0.25 mm to 0.55 mm, in some examples, 0.3 mm to 0.5 mm, in some examples, 0.35 mm to 0.45 mm, in some examples, 0.025 mm to 0.4 mm, in some examples, 0.025 mm to 0.35 mm, in some examples, 0.03 mm to 0.35 mm, in some examples, 0.04 mm to 0.13 mm.

In some examples, stereolithographically printing comprises creating a virtual model, for example, a 3D computer-aided design (CAD) model, of the device to be printed; converting the virtual model into thin layers and instructing a stereolithography apparatus to stereolithographically print the device.

In some examples, washing the printed intraocular device removes the un-polymerised stereolithography composition from the surface of the printed intraocular device. In some examples, the washing is performed by using any solvent. The solvent may be a polar solvent. The solvent may be selected from aqueous solvents and alkanol solvents. The solvent may be selected from water, methanol, ethanol, propanol, isopropyl alcohol, butanol, pentanol and hexanol. In some examples, the solvent may be selected form water, methanol, ethanol, propanol and isopropyl alcohol. In some examples, the solvent may be isopropyl alcohol. In some examples, the solvent may comprise a surfactant, a buffer or a combination thereof. In some examples, the solvent may be an aqueous solvent comprising a surfactant, such as a detergent. In some examples, the buffer may be a borate buffer.

In some examples, the printed intraocular device is heated to fully cure the stereolithography composition. In some examples, the heat is applied by placing the printed intraocular device in an oven or by using an IR lamp. In some examples, the heat is applied under a vacuum, for example, in a vacuum oven.

The heating may be to a temperature and for a duration sufficient to fully cure the stereolithography composition. The heating and irradiation may in combination be to a temperature and for a duration sufficient to fully cure the stereolithography composition.

In some examples, the heating may be to a temperature of 50° C. or more, in some examples, 55° C. or more, in some examples, 60° C. or more, in some examples, 65° C. or more, in some examples, 70° C. or more, in some examples, 75° C. or more, in some examples, 80° C. or more, in some examples, 85° C. or more, in some examples, 90° C. or more, in some examples, 95° C. or more, in some examples, 100° C. or more. In some examples, the heating may be to a temperature of less than the melting point of the printed intraocular device. In some examples, the heating may be to a temperature of 100° C. or less, in some examples, 95° C. or less, in some examples, 90° C. or less, in some examples, 85° C. or less, in some examples, 80° C. or less, in some examples, 75° C. or less, in some examples, 70° C. or less, in some examples, 65° C. or less, in some examples, 60° C. or less, in some examples, 55° C. or less, in some examples, 50° C. or less. In some examples, the heating may be to a temperature of from 50° C. to 100° C., in some examples, 55° C. to 95° C., in some examples, 60° C. to 90° C., in some examples, 65° C. to 85° C., in some examples, 70° C. to 80° C., in some examples, 70° C. to 75° C.

In some examples, the heating may be for 4 hours or more, in some examples, 5 h or more, in some examples, 6 h or more, in some examples, 7 h or more, in some examples, 8 h or more, in some examples, 9 h or more, in some examples, 10 h or more, in some examples, 11 h or more, in some examples, 12 h or more, in some examples, 13 h or more, in some examples, 14 h or more, in some examples, 15 h or more, in some examples, 16 h or more, in some examples, 17 h or more, in some examples, 18 h or more, in some examples, 19 h or more, in some examples, 20 h or more, in some examples, 21 h or more, in some examples, 22 h or more, in some examples, 23 h or more, in some examples, 24 h or more. In some examples, the heating may be for 24 hours or less, in some examples, 23 h or less, in some examples, 22 h or less, in some examples, 21 h or less, in some examples, 20 h or less, in some examples, 19 h or less, in some examples, 18 h or less, in some examples, 17 h or less, in some examples, 16 h or less, in some examples, 15 h or less, in some examples, 14 h or less, in some examples, 13 h or less, in some examples, 12 h or less, in some examples, 11 h or less, in some examples, 10 h or less, in some examples, 9 h or less, in some examples, 8 h or less, in some examples, 7 h or less, in some examples, 6 h or less, in some examples, 5 h or less, in some examples, 4 h or less. In some examples, the heating may be for from 4 hours to 24 hours, in some examples, 5 h to 23 h, in some examples, 6 h to 22 h, in some examples, 7 h to 21 h, in some examples, 8 h to 20 h, in some examples, 9 h to 19 h, in some examples, 10 h to 18 h, in some examples, 11 h to 17 h, in some examples, 8 h to 16 h, in some examples, 9 h to 15 h, in some examples, 10 h to 14 h, in some examples, 11 h to 13 h, in some examples, 10 h to 12 h, in some examples, 12 h to 15 h.

In some examples, the irradiation occurs for 1 min or more, in some examples, 5 min or more, in some examples, 10 min or more, in some examples, 15 min or more, in some examples, 20 min or more, in some examples, 25 min or more, in some examples, 30 min or more, in some examples, 35 min or more, in some examples, 40 min or more, in some examples, 45 min or more, in some examples, 50 min or more, in some examples, 55 min or more, in some examples, 1 h or more. In some examples, the irradiation occurs for 1 h or less, in some examples, 55 min or less, in some examples, 50 min or less, in some examples, 45 min or less, in some examples, 40 min or less, in some examples, 35 min or less, in some examples, 30 min or less, in some examples, 25 min or less, in some examples, 20 min or less, in some examples, 15 min or less, in some examples, 10 min or less, in some examples, 5 min or less, in some examples, 1 min or less. In some examples, the irradiation occurs for 1 min to 1 h, in some examples, 5 min to 55 min, in some examples, 10 min to 50 min, in some examples, 15 min to 45 min, in some examples, 20 min to 40 min, in some examples, 25 min to 35 min, in some examples, 30 min to 35 min, in some examples, 25 min to 30 min.

In some examples, the irradiation is UV irradiation. In some examples, the irradiation is at the same wavelength as the irradiation used in the stereolithographic printing. In some examples, the irradiation is applied by using a laser, optionally a UV laser.

In some examples, after the application of heat and irradiation to fully cure the stereolithography composition, the method further comprises additional processing steps, for example, lathing. In some examples, after the stereolithography composition is fully cured, the cured stereolithography composition is further processable, that is, can be subjected to further processing, such as lathing.

The intraocular device may be non-cytotoxic and biocompatible. In some examples, components of the stereolithography composition are non-cytotoxic. In some examples, the components of the stereolithography composition are non-cytotoxic towards lens epithelial cell lines (for example FHL-124) after 48 h and 96 h. Cytotoxicity may be measured relative to the same cell line in the absence of the stereolithography composition and/or the intraocular device. The intraocular device may be considered non-cytotoxic if the amount of LDH release by cells, for example, lens epithelial cells, after 48 h and/or 96 h in the presence of the intraocular device is not significantly greater than the amount of LDH release after the same time period in the absence of the intraocular device.

In some examples, the intraocular device may be an intraocular lens, a keratoprosthesis, intraocular ring, corneal inlay (also called an intracorneal implant), or aqueous shunts/glaucoma filtration devices. In some examples, the intraocular device is an intraocular lens.

In some examples, the intraocular device is capable of being rolled or folded. In some examples, the intraocular device is a foldable intraocular device. In some examples, the intraocular lens is a lens capable of being rolled or folded. In some examples, the intraocular lens is a foldable intraocular lens.

The intraocular lens may comprise an optic and at least one haptic. The intraocular lens may comprise two haptics. The optic is the portion of the intraocular lens which serves as the lens and the haptic(s) is(are) attached to the optic and maintains the optic in its proper place in the eye. The optic and the haptic(s) may be of the same or different material. A multi-piece lens is so called because the optic and the haptic(s) are made separately and then the haptic(s) is(are) attached to the optic. In a single piece lens, the optic and the haptic(s) are formed out of one piece of material. In this invention, a single piece lens is preferred.

In some examples, the optic is a convex shape. In some examples, the thickness of the optic is constant across the diameter of the optic.

The haptic may have a plate design, an encircling haptic design or an open loop haptic design. In some examples, the haptic has an open loop haptic design.

In some examples, the intraocular lens comprises at least two haptics. In some examples, the intraocular lens may have the shape described in U.S. Pat. No. 5,716,403, which is incorporated by reference herein.

The intraocular lens may have a length of between about 10.5 mm and about 14 mm, wherein the length is the longest dimension of the intraocular lens (also known as the haptic-to-haptic length). In some examples, the intraocular lens may have a length of between about 12.5 mm and about 13 mm. In some examples, the intraocular lens may have a length of about 13 mm.

The optic may have an anterior side and a posterior side. The optic may have a diameter of between about 4.5 mm and about 7 mm, optionally about 5.5 mm to about 6 mm, optionally about 6 mm. The optic may be elliptical or oval. The thickness of the optic will vary depending on the dioptric power desired and the index of refraction of the material used, but may be between about 0.4 mm and about 1.5 mm.

The haptic(s) may (each) contain a gusset, an elbow, and a distal portion wherein the width of the distal portion may vary along its length. As used herein, the width of the distal portion may be the width of the distal portion when viewed from above looking along the optical axis of the intraocular lens. As used herein, the length of the distal portion may be the length as measured by following the centre line of the width of the distal portion rather than the straight line distance between the two ends of the distal portion. The width of the distal portion is a dimension of the distal portion that is perpendicular to the length of the distal portion. The gusset may be connected to the distal portion by the elbow of the haptic. The gusset is the portion of the haptic connecting the optic to the haptic. The elbow and distal portion may have uniform thickness (wherein the thickness of the intraocular lens is in the direction perpendicular to the length of the intraocular lens), which may be between about 0.3 mm and about 0.6 mm, optionally between about 0.4 mm and about 0.5 mm, optionally, about 0.43 mm. The gusset may have a thickness that is reduced towards the anterior side of the optic and the thickness of the gusset may be between about 0.15 mm and about 0.6 mm, optionally between about 0.25 mm and about 0.35 mm, optionally about 0.3 mm. The gusset generally extends from the edge of the optic such that the distance between the optical axis of the optic and the end of the reduced thickness portion is between 3 mm and 4.5 mm, optionally 3.5 mm. The distal portion may have a length of about 4 mm to about 5 mm, optionally about 4.65 mm. The elbow creates a hinge allowing the haptic to flex while minimizing buckling and vaulting of the optic. The variation of the width of the distal portion along its length may be such that the wider portion of the distal portion is closest to the elbow such that the stiffness of the haptic is increased at the point just past the elbow thereby increasing the strength of the haptic portion at a critical stress point.

In another example, the intraocular lens may comprise an optic and a ring haptic. In some examples, the ring haptic may be a circular fenestrated 360° ring haptic. In some examples, the ring haptic may be connected to the optic by spokes. In some examples, the haptic may comprise an anterior haptic ring and a posterior haptic ring. In some examples, the anterior haptic ring and the posterior haptic ring are separated, for example, by 2 mm. In some examples, the optic is suspended between two complete haptic rings connected by a pillar. In some examples, the space between the optic and the haptic rings is fenestrated with slits. In some examples, the intraocular lens may have a circumference of between 20 mm and 23 mm, for example, between 21 mm and 22 mm, for example, about 21.6 mm. In some examples, the intraocular lens may have a diameter of between 7 mm and 10 mm, for example, between 8 mm and 9 mm, for example about 8.8 mm. In some examples, the optic may have a diameter of between 4 mm and 7 mm, for example, between 5 mm and 6 mm, for example, about 5.8 mm.

Uses and Methods of Using the Intraocular Device.

In an aspect, the stereolithography composition, for example, once cured, may be used in the treatment of cataracts. In another aspect, the stereolithographically printed intraocular device may be used in the treatment of cataracts. In an additional aspect, the stereolithography composition having been stereolithographically printed in the form of an intraocular device may be used in the treatment of cataracts. The intraocular device used in the treatment of cataracts may be an intraocular lens.

As used herein, a stereolithographically printed intraocular device may be termed a stereolithographically printed composition.

For the avoidance of all doubt, the intraocular device may be the stereolithographically printed stereolithography composition.

In a further aspect, there is provided a method of treating cataracts comprising implanting a stereolithographically printed intraocular device. The stereolithographically printed intraocular device may be implanted into an eye, optionally, into the capsular bag of an eye. The intraocular device used in the treatment of cataracts may be an intraocular lens.

The implantation may be by surgical injector.

Prior to implantation of the stereolithographically printed intraocular lens, the cataract containing lens may be removed from the eye, for example, by phacoemulsification.

The following numbered paragraphs define particular embodiments of the present disclosure:

1. A stereolithography composition for printing intraocular devices, the stereolithography composition comprising:
   a photoinitiator;
   a monofunctional aryl acrylate monomer, wherein the acrylate group of the monofunctional aryl acrylate monomer is of the formula —O—(C=O)—CH=CH$_2$; and
   a multifunctional methacrylate cross-linker,
   wherein the monofunctional aryl acrylate monomer is present in the composition in a greater amount than the multifunctional methacrylate cross-linker.
2. A stereolithography composition according to paragraph 1, wherein the multifunctional methacrylate cross-linker comprises 2, 3 or 4 methacrylate groups.
3. A stereolithography composition according any preceding paragraph, wherein the monofunctional aryl acrylate monomer constitutes 50 wt. % or more of the stereolithography composition.
4. A stereolithography composition according to any preceding paragraph, wherein the multifunctional methacrylate cross-linker constitutes 25 wt. % or less of the stereolithography composition.
5. A stereolithography composition according to any preceding paragraph, wherein the photoinitiator constitutes 5 wt. % or less of the stereolithography composition.
6. A stereolithography composition according to any preceding paragraph, wherein the monofunctional aryl acrylate monomer is of the formula R—O—(C=O)—CH=CH$_2$, wherein R is —(CH$_2$)$_m$YAr, wherein m is 0 to 6;
   Y is nothing, O, S, NR', wherein R' is H, CH$_3$, C$_n$H$_{2n+1}$, iso-OC$_3$H$_7$, C$_6$H$_5$, or CH$_2$C$_6$H$_5$, wherein n is 1 to 10; and
   Ar is any aromatic ring which may be unsubstituted or substituted with H, CH$_3$, C$_2$H$_5$, n-C$_3$H$_7$, iso-C$_3$H$_7$, OCh$_3$, C$_6$H$_{11}$, Cl, Br, C$_6$H$_5$, or CH$_2$C$_6$H$_5$.
7. A stereolithography composition according to paragraph 6, wherein R is —(CH$_2$)$_2$OPh.
8. A stereolithography composition according to any preceding paragraph, wherein the multifunctional methacrylate cross-linker is of the formula CH$_2$=CHMe-(C=O)—O—R"—O—(C=O)—CHMe=CH$_2$ wherein R" is selected from alkyl, polyalkyl and polyether.
9. A stereolithography composition according to paragraph 8, wherein R" is polyether.
10. A stereolithography composition according to any of paragraphs 8 or 9, wherein the multifunctional methacrylate cross-linker has a number average molecular weight of 500 or more.
11. A stereolithography composition according to any of paragraphs 8 to 10, wherein the multifunctional methacrylate cross-linker has a number average molecular weight of 1000 or less.
12. A stereolithography composition according to any of paragraphs 8 to 11, wherein the multifunctional methacrylate cross-linker is polyethylene glycol dimethacrylate.
13. A stereolithography composition according to any preceding paragraph, wherein the photoinitiator is selected from diphenyl(2,4,6-trimethylbenzoyl)phosphine oxide (TPO), an acetophenone derivative, benzophenone, phenylbis(2,4,6-trimethylbenzoyl)phosphine oxide (BAPO), and 2-(4-methoxystyryl)-4,6-bis(trichloromethyl)-1,3,5-triazine.
14. A method of producing intraocular devices, the method comprising:
    stereolithographically printing intraocular devices using a stereolithography composition comprising:
      a photoinitiator;
      a monofunctional aryl acrylate monomer, wherein the acrylate group of the monofunctional aryl acrylate monomer is of the formula —O—(C=O)—CH=CH$_2$; and
      a multifunctional methacrylate cross-linker, and
      wherein the monofunctional aryl acrylate monomer is present in the composition in a greater amount than the multifunctional methacrylate cross-linker;
    washing the printed intraocular device; and
    applying heat and irradiation to fully cure the stereolithography composition.
15. The method according to paragraph 14, wherein the irradiation occurs for 30 min or more.
16. The method according to paragraph 14 or 15, wherein the heat is applied for 4 hours or more.
17. The method according to any of paragraphs 14 to 16, wherein the heat is applied for 24 hours or less.
18. The method according to any of paragraphs 14 to 17, wherein heating is heating to a temperature of 50° C. or more.
19. The method according to any of paragraphs 14 to 18, wherein heating is heating to a temperature of 100° C. or less.
20. The method according to any of paragraphs 14 to 19, wherein the stereolithography composition is a stereolithography composition according to any of paragraphs 2 to 13.
21. The method according to any of paragraphs 14 to 20, wherein the intraocular device is an intraocular lens.
22. The method according to paragraph 21, wherein the intraocular lens comprises an optic and at least one haptic.
23. A stereolithographically printed intraocular device formed by the method of any one of paragraphs 14 to 22.
24. A stereolithographically printed intraocular device according to paragraph 23 for use in the treatment of cataracts.
25. A stereolithography composition according to any of paragraphs 1 to 14, having been stereolithographically printed to form an intraocular device, for use in the treatment of cataracts.

Examples

Generation of the Virtual Model

The CAD file for the IOLs was generated using Blender 3D modelling software (Stichting Blender Foundation, Amsterdam, The Netherlands). The virtual model was based on the shape of a commercially available IOL, the Alcon AcrySof® (Alcon, Texas, USA) IOL, which is the IOL with lowest PCO rates available in the market. Thus, an image of this IOL was used as a template to generate the 3D virtual model. The virtual model was created such that, once stereolithographically printed, the IOL would have a haptic-to-haptic length of 13 mm, an optic diameter of 6 mm and a thickness of 0.9 mm (with both the optic and haptics having the same thickness). The virtual model was then exported as a stereolithography file (STL) and processed on the PreForm software (Formlabs Inc., Somerville, MA, USA) prior to stereolithographic printing. The layer thickness for printing was set at 0.05 mm/layer and the type of laser selected was the one for Black resin, which has a wavelength of 405 nm.

Stereolithography Composition

Composition 1

A stereolithography composition for printing intraocular devices was provided by combining 2-phenoxyethyl acrylate (93 wt. %; TCI Chemicals, >93% purity), poly(ethylene glycol) dimethacrylate (7 wt. %; Sigma Aldrich, $M_n$ 750 g/mol) and diphenyl(2,4,5-trimethylbenzoyl)phosphine oxide (1 wt. %; TCI Chemicals). The three components were mixed in a round-bottom flask, stirred until complete dissolution had been achieved and purged with nitrogen.

This composition resulted in stereolithographically printed intraocular lenses with optimal flexibility and mechanical strength after a post-printing curing procedure of 1 h UV and heating overnight at 70° C. under vacuum.

Composition 2

A stereolithography composition for printing intraocular devices was provided by combining 2-phenoxyethyl acrylate (94 wt. %; TCI Chemicals, >93% purity), poly(ethylene glycol) dimethacrylate (6 wt. %; Sigma Aldrich, $M_n$ 750 g/mol) and diphenyl(2,4,5-trimethylbenzoyl)phosphine oxide (1 wt. %; TCI Chemicals). The three components were mixed in a round-bottom flask, stirred until complete dissolution had been achieved and purged with nitrogen.

This composition resulted in stereolithographically printed intraocular lenses with lower mechanical strength than composition 1 after a post-printing curing procedure of 1 h UV and heating overnight at 70° C. under vacuum.

Composition 3

A stereolithography composition for printing intraocular devices was provided by combining 2-phenoxyethyl acrylate (96 wt. %; TCI Chemicals, >93% purity), poly(ethylene glycol) dimethacrylate (4 wt. %; Sigma Aldrich, $M_n$ 750 g/mol) and diphenyl(2,4,5-trimethylbenzoyl)phosphine oxide (1 wt. %; TCI Chemicals). The three components were mixed in a round-bottom flask, stirred until complete dissolution had been achieved and purged with nitrogen.

This composition resulted in stereolithographically printed intraocular lenses with lower mechanical strength than composition 2. Additionally, the edges of the intraocular lenses were over-cured after a post-printing curing procedure of 1 h UV and heating overnight at 70° C. under vacuum.

Reference Composition

A stereolithography composition for printing intraocular devices was provided by combining 2-hydroxyethyl acrylate (82 wt. %; Sigma-Aldrich, purity of 96%), methyl acrylate (16 wt. %; Sigma-Aldrich, purity of 99%), poly(ethylene glycol) diacrylate (1.5 wt. %; Sigma-Aldrich, purity of 99%), $M_n$ 700 g/mol) and diphenyl(2,4,5-trimethylbenzoyl) phosphine oxide (0.5 wt. %; TCI Chemicals). The three components were mixed in a round-bottom flask, stirred until complete dissolution had been achieved and purged with nitrogen.

This composition resulted in stereolithographically printed intraocular lenses with good flexibility but not enough mechanical strength and with a non-optimal resolution after a post-printing curing procedure of 1 h UV and heating overnight at 70° C. under vacuum.

Stereolithographic Printing

The stereolithography composition was poured into the vat of a Form 2 stereolithography printer (Formlabs Inc., Somerville, MA, USA). The STL file (see above) was uploaded to the printer. Stereolithographic printing of the intraocular device was performed without the build platform of the Form 2 printer. Instead, the first layer of the IOL was printed and then a glass slide was placed on top of the first layer and the printing was continued until the sixth layer had been printed (polymerised), forming a printed intraocular lens. The glass slide was used to obtain an IOL with a smooth surface. The printed IOL was washed with isopropanol and then irradiated with UV light (A=405 nm) for 1 h and heated overnight in a vacuum oven at 70° C.

Tests

Assessment of Post-Printing Curing Efficiency

The efficacy of post-printing curing in eliminating unreacted monomers left within the polymeric structure of the IOL was evaluated by $^1$H NMR spectroscopy. IOLs that had been irradiated with UV light for 1 or 2 hours and subjected to heating at 70° C. for 0 to 12 h (12 h=overnight) were incubated in 800 µL of D-chloroform (Sigma Aldrich) for 1 h. The incubation medium was filtered and the eluent was analysed by $^1$H NMR spectroscopy (at 25° C.; Brucker 400 MHz spectrometer) to detect any unreacted monomers that may have been left within the polymeric structure of the IOL after printing. FIG. 1 shows the spectra obtained for IOLs produced by stereolithographically printing stereolithography composition 1. The intensity of the signal at 4.8 to 5.2 ppm, which is produced by the alkene groups of remaining unreacted monomers, is reduced after longer post-printing curing times.

Evaluation of Cytotoxicity

FHL-124 cells (a foetal human lens cell line) were cultured at 37° C. and in an atmosphere containing 5 vol. % $CO_2$ (with $CO_2$ being pumped into an incubator containing air and the reactants) until confluent areas of cells had formed (generally after three days) in Eagle's Minimum Essential Medium (EMEM; available from Pan Biotech; contains Earle's balanced salt solution (EBSS) and non-essential amino acid (NEAA)), supplemented with 5 vol. % foetal calf serum and 50 mg/L gentamicin. Additionally, the EMEM used herein was supplemented with L-glutamine (1 vol. %). On the third day (or after confluent areas had formed), the medium was replaced by a serum-free EMEM. After 24 h, the stereolithographically printed IOLs were added to the culture medium by pinning the IOLs on top of the cells.

The tested stereolithographically printed IOLs were stereolithographically printed by using stereolithography composition 1. The stereolithographically printed IOLs were divided into six groups, with each group containing four IOLs in order to achieve statistically significant results. Each of the groups contained IOLs that had been subjected to different amounts of the post-curing process. The six groups were: not post-cured; post-cured with UV light for 1 h; and post-cured with UV light for 1 h and heated for either 3 h, 4 h, 8 h or overnight. A negative control group without an IOL was also tested.

Once the IOLs were pinned down on the Petri dishes, the serum free medium was replaced with fresh serum-free medium. This was done to remove any cells that had died as a consequence of the mechanical stress imposed by the pinning process, and which would otherwise bias the results of the experiment. The Petri dishes were maintained at 35° C. and 5 vol. % $CO_2$ in an incubator. After 48 h, the liquid was collected into 1.5 mL Eppendorf tubes to assess the cytotoxicity at 48 h. The serum-free EMEM in the Petri dishes was refreshed and the Petri dishes were maintained at 35° C. and 5 vol. % $CO_2$ in an incubator for a further 48 h before the liquid was collected into 1.5 mL Eppendorf tubes to assess the cytotoxicity after 96 h. The cytotoxicity was assessed by performing a lactate dehydrogenase (LDH) assay (Roche, Basel, Switzerland). Briefly, 100 µL of liquid media was transferred from each Eppendorf tube to a 96-well plate, repeating this procedure four times for each IOL group. Then, 100 µL of LDH assay reaction mixture (provided as part of the LDH assay kit available from Roche and used as directed, including as a 1:45 mixture of the two solutions) was added to each well and the plate was incubated for 10 min in the dark at room temperature. The reaction was then stopped by adding 50 µL of the stop solution (1N HCl) and the absorbance at 490 nm was measured on a BMG Labtech Fluostar Omega spectrophotometer.

Physico-Chemical Characterisation of the Stereolithographically Printed IOLs

Thermal analysis was performed in order to evaluate the glass transition temperature ($T_g$) and thermal stability of the IOLs.

Figure 3:
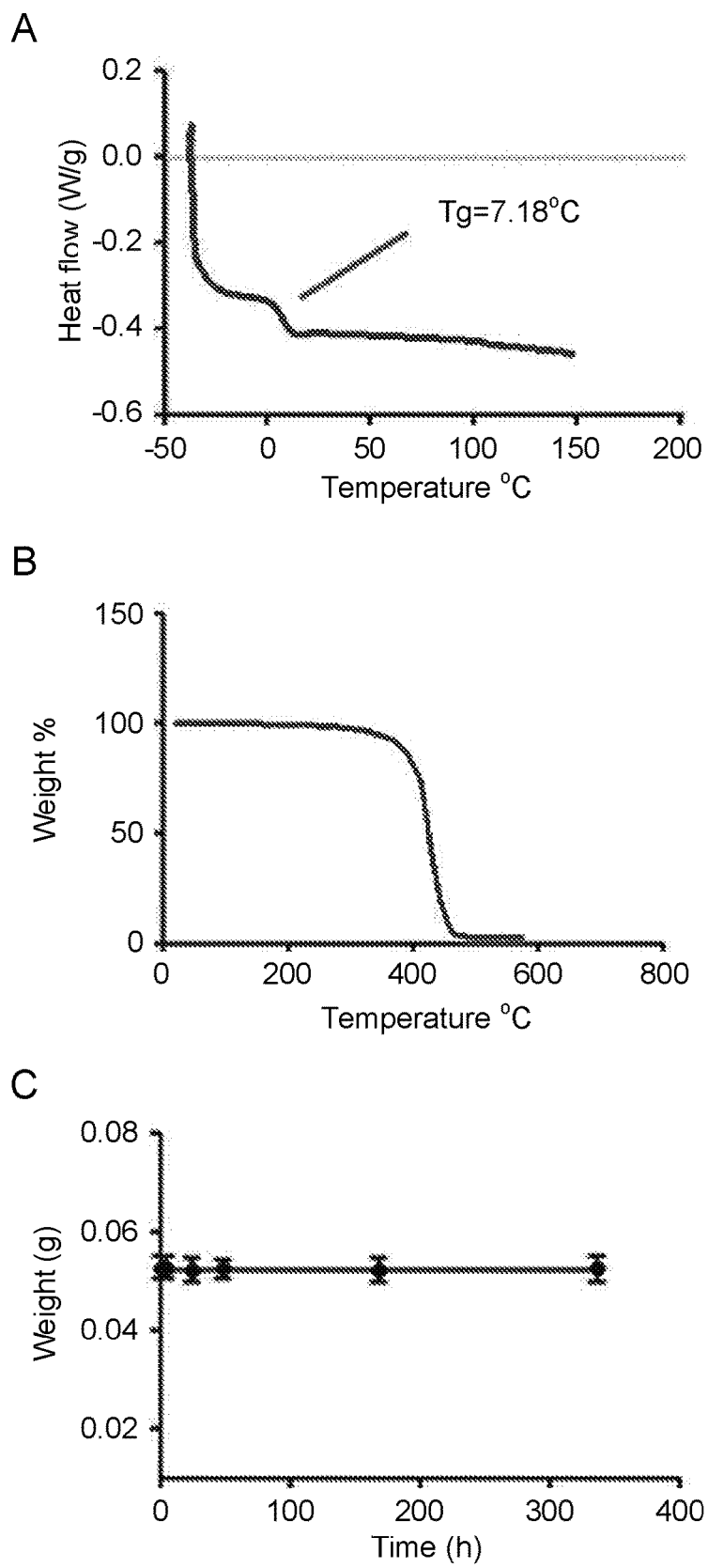
FIG. 3 shows a DSC thermogram obtained for the second heating cycle of an IOL (A), a thermogravimetric analysis thermogram (B) and results of a swelling test (C).

The glass transition temperature was elucidated by DSC analysis in a DSC 2500 instrument (TA instruments, New Castle, USA). This was done by cutting a small piece of polymer (1-3 mg) from a post-printing cured IOL and pressing it into an aluminium DSC pan before placing it in the sample tray for analysis. The polymer was then subjected to a first heating cycle of from −50° C. to 150° C., followed by a cooling scan back to −50° C., followed by a second heating cycle to 150° C. Heating and cooling cycles were both performed at a heating rate of 10° C./min under a constant nitrogen flow of 50 mL/min. The $T_g$ was calculated from the DSC thermogram of the second heating cycle as the temperature of the mid-point of the decline in the heat capacity that occurs during this thermal event. A DSC thermogram for the polymer in IOLs produced from stereolithography composition 1 after 1 h UV and heating at 70° C. overnight, showing a $T_g$ of 7.18° C., is shown in FIG. 3A.

The thermal stability of the IOL material was evaluated by Thermogravimetric Analysis (TGA). This test was performed in a TGA 5500 (TA Instruments, New Castle, USA) under a nitrogen atmosphere. The sample was heated form 25° C. to 500° C. at a heating rate of 10° C./min. A thermogram for the polymer in IOLs produced from stereolithography composition 1 after 1 h UV and heating at 70° C. overnight is shown in FIG. 3B.

The absorption of water by the IOL was measured by performing a swelling test. Four IOLs were incubated in 0.5 mL PBS 1× (pH 7.4) at 35° C. for 1 month. The weight was monitored after 4 h, 24 h, 48 h, one week, two weeks, and 1 month. A graph of the weight of IOLs produced from stereolithography composition 1 after 1 h UV and heating at 70° C. overnight is shown in FIG. 3C. The weight of the IOL remained constant over a prolonged period, indicating that the aromatic group containing polymer material is fairly hydrophobic and water cannot penetrate into the bulk of the stereolithographically printed IOL. This is an important advantage over IOLs fabricated by lathing techniques. The lathing techniques are known to create a void that can be filled with aqueous humour after implantation, affecting the contrast sensitivity of the IOL.

Morphological Evaluation of the IOLs

Figure 4:
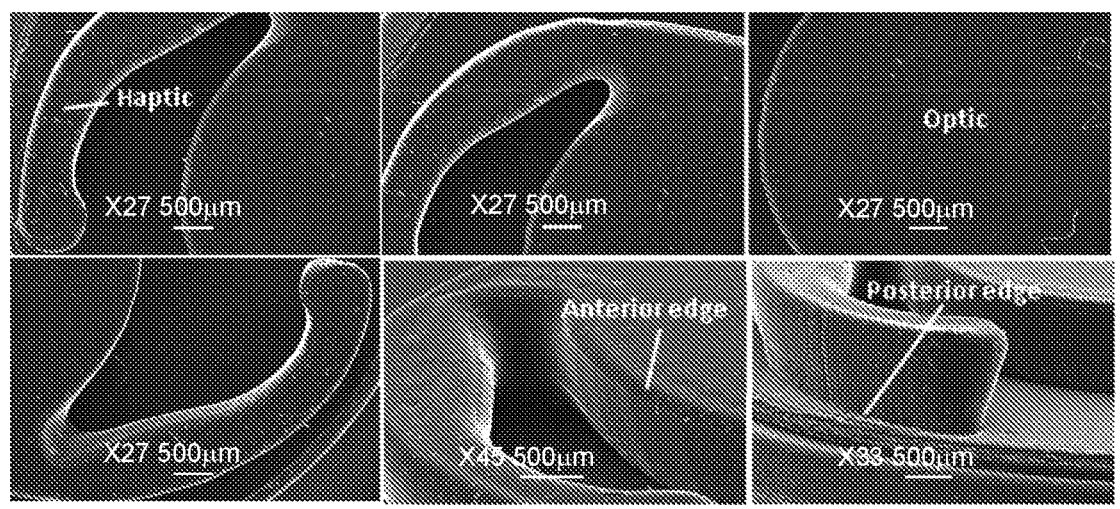
FIG. 4 shows SEM images of IOLs after sputter coating with gold.

SEM images of IOLs produced from stereolithography composition 1 after 1 h UV and heating at 70° C. overnight to evaluate their morphology and the sharpness of their edges. After sputter coating the IOLs with gold, SEM images were generated with a JEOL HSM 5900 LV microscope with a 20 kV accelerating voltage. The SEM images are shown in FIG. 4.

Implantation of the IOL into a Human Capsular Bag In Vitro

Figure 5:
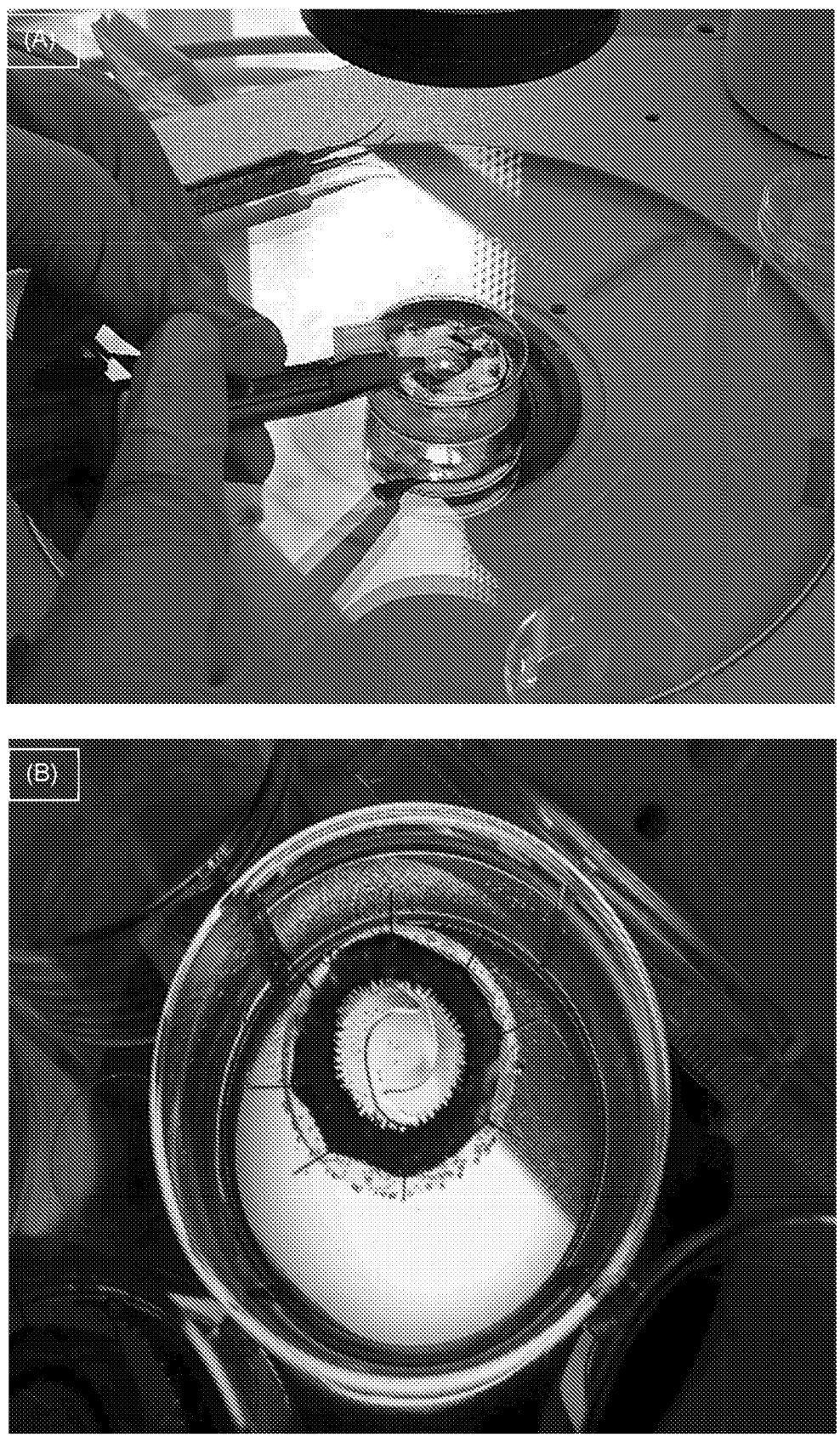
FIG. 5 shows photographs of the implantation of the IOL into the capsular bag of a human eye with a surgical injector (A) and the IOL implanted in the capsular bag (B).

Two IOLs produced from stereolithography composition 1 after 1 h UV and heating at 70° C. overnight were implanted into a capsular bag obtained from a human donor eye. Briefly, a cataract operation was performed on the lens in the capsular bag of a human eye to remove the fibres it contains. The surgical technique used was based on the extracapsular cataract extraction procedure. Thus, a small capsulorhexis was made on the anterior capsule and the lens fibres were removed through it by hydro-expression (see Liu et al., *Investigative Ophthalmology & Visual Science*, April 1996, vol. 37, 906-914). The foldable IOL produced from stereolithography composition 1 after 1 h UV and heating at 70° C. overnight was implanted into the capsular bag with a suitable injector. Photographs of the implantation procedure and implanted IOL are shown in FIG. 5.

Statistical Analysis

Data sets obtained in the experiments above were analysed by using GraphPad Prism software. One-way ANOVA was used to compare the mean of the experimental groups analysed in the LDH assays. Bartlett's test was used to assess the equality of variance in the different groups. Moreover, a t-test was performed to compare the mean value of the "overnight post-printing cured" group with that of the control.

The invention claimed is:

1. A stereolithography composition for printing intraocular devices, the stereolithography composition comprising:
   a photoinitiator;
   a monofunctional aryl acrylate monomer, wherein the acrylate group of the monofunctional aryl acrylate monomer is of the formula —O—(C=O)—CH=$CH_2$; and
   a multifunctional methacrylate or acrylate cross-linker,
   wherein the monofunctional aryl acrylate monomer is present in the composition in a greater amount than the multifunctional methacrylate or acrylate cross-linker.

2. A stereolithography composition according to claim 1, wherein the multifunctional methacrylate or acrylate cross-linker comprises 2, 3 or 4 methacrylate groups.

3. A stereolithography composition according to claim 1, wherein the monofunctional aryl acrylate monomer constitutes 50 wt. % or more of the stereolithography composition.

4. A stereolithography composition according to claim 1, wherein the multifunctional methacrylate or acrylate cross-linker constitutes 25 wt. % or less of the stereolithography composition.

5. A stereolithography composition according to claim 1, wherein the photoinitiator constitutes 5 wt. % or less of the stereolithography composition.

6. A stereolithography composition according to claim 1, wherein the monofunctional aryl acrylate monomer is of the formula R—O—(C=O)—CH=CH$_2$, wherein R is —(CH$_2$)$_m$YAr, wherein m is 0 to 6;

Y is nothing, O, S, NR', wherein R' is H, CH$_3$, C$_n$H$_{2n+1}$, iso-OC$_3$H$_7$, C$_6$H$_5$, or CH$_2$C$_6$H$_5$, wherein n is 1 to 10; and Ar is any aromatic ring which may be unsubstituted or substituted with H, CH$_3$, C$_2$H$_5$, n-C$_3$H$_7$, iso-C$_3$H$_7$, OCh$_3$, C$_6$H$_{11}$, Cl, Br, C$_6$H$_5$, or CH$_2$C$_6$H$_5$.

7. A stereolithography composition according to claim 6, wherein R is —(CH$_2$)$_2$OPh.

8. A stereolithography composition according to claim 1, wherein the multifunctional methacrylate or acrylate cross-linker is a multifunctional methacrylate cross-linker of the formula CH$_2$=CHMe-(C=O)—O—R"—O—(C=O)—CHMe=CH$_2$ wherein R" is selected from alkyl, polyalkyl and polyether.

9. A stereolithography composition according to claim 8, wherein R" is polyether.

10. A stereolithography composition according to claim 8, wherein the multifunctional methacrylate cross-linker has a number average molecular weight of 500 or more and 1000 or less.

11. A stereolithography composition according to claim 8, wherein the multifunctional methacrylate cross-linker is polyethylene glycol dimethacrylate.

12. A stereolithography composition according to claim 1, wherein the photoinitiator is selected from diphenyl(2,4,6-trimethylbenzoyl)phosphine oxide (TPO), an acetophenone derivative, benzophenone, phenylbis(2,4,6-trimethylbenzoyl)phosphine oxide (BAPO), and 2-(4-methoxystyryl)-4,6-bis(trichloromethyl)-1,3,5-triazine.

13. A method of producing intraocular devices, the method comprising:

stereolithographically printing intraocular devices using a stereolithography composition comprising:

a photoinitiator;

a monofunctional aryl acrylate monomer, wherein the acrylate group of the monofunctional aryl acrylate monomer is of the formula —O—(C=O)—CH=CH$_2$; and a multifunctional methacrylate or acrylate cross-linker, and wherein the monofunctional aryl acrylate monomer is present in the composition in a greater amount than the multifunctional methacrylate or acrylate cross-linker;

washing the printed intraocular device; and applying heat and irradiation to fully cure the stereolithography composition.

14. The method according to claim 13, wherein the irradiation occurs for 30 min or more.

15. The method according to claim 13, wherein the heat is applied for 4 hours or more and for 24 hours or less.

16. The method according to claim 13, wherein heating is heating to a temperature of 50° C. or more and 100° C. or less.

17. The method according to claim 13, wherein the intraocular device is an intraocular lens.

18. The method according to claim 17, wherein the intraocular lens comprises an optic and at least one haptic.

19. A stereolithographically printed intraocular device formed by the method of claim 13.

20. A stereolithography composition according to claim 1, having been stereolithographically printed to form an intraocular device, for use in the treatment of cataracts.

* * * * *